United States Patent
Lafontaine

(10) Patent No.: US 8,512,399 B2
(45) Date of Patent: *Aug. 20, 2013

(54) VALVE APPARATUS, SYSTEM AND METHOD

(75) Inventor: Daniel M. Lafontaine, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 255 days.

This patent is subject to a terminal disclaimer.

(21) Appl. No.: 12/648,221

(22) Filed: Dec. 28, 2009

(65) Prior Publication Data

US 2010/0100173 A1  Apr. 22, 2010

Related U.S. Application Data

(63) Continuation of application No. 11/107,162, filed on Apr. 15, 2005, now Pat. No. 7,722,666.

(51) Int. Cl.
*A61F 2/24* (2006.01)

(52) U.S. Cl.
USPC .................. 623/2.11; 623/2.12; 623/2.17

(58) Field of Classification Search
USPC ................. 623/2.11, 2.12, 2.14, 2.17, 2.18, 623/2.38, 1.24
See application file for complete search history.

(56) References Cited

U.S. PATENT DOCUMENTS

| | | | |
|---|---|---|---|
| 3,671,979 A | 6/1972 | Moulopoulos | 3/1 |
| 4,291,420 A | 9/1981 | Reul | 3/1.5 |
| 4,787,901 A | 11/1988 | Baykut | 623/2 |
| 4,872,874 A | 10/1989 | Taheri | 623/1 |
| 4,935,030 A | 6/1990 | Alonso | 623/2 |
| 4,994,077 A | 2/1991 | Dobben | 623/2 |
| 5,002,567 A | 3/1991 | Bona et al. | 623/2 |
| 5,141,491 A | 8/1992 | Bowald | 604/22 |
| 5,163,953 A | 11/1992 | Vince | 623/2 |
| 5,219,355 A | 6/1993 | Parodi et al. | 606/191 |
| 5,254,127 A | 10/1993 | Wholey et al. | 606/153 |
| 5,327,774 A | 7/1994 | Nguyen et al. | 73/37 |
| 5,332,402 A | 7/1994 | Teitelbaum | 623/2 |
| 5,370,685 A | 12/1994 | Stevens | 623/2 |
| 5,411,552 A | 5/1995 | Anderson et al. | 623/2 |
| 5,469,868 A | 11/1995 | Reger | 128/898 |
| 5,480,423 A | 1/1996 | Ravenscroft et al. | 623/1 |
| 5,500,014 A | 3/1996 | Quijano et al. | 623/2 |
| 5,545,214 A | 8/1996 | Stevens | 623/2 |
| 5,554,185 A | 9/1996 | Block et al. | 623/2 |
| 5,643,208 A | 7/1997 | Parodi | 604/96 |
| 5,693,087 A | 12/1997 | Parodi | 623/1 |
| 5,713,953 A | 2/1998 | Vallana et al. | 623/2 |
| 5,716,370 A | 2/1998 | Williamson, IV et al. | 606/153 |
| 5,735,859 A | 4/1998 | Fischell et al. | 606/108 |

(Continued)

FOREIGN PATENT DOCUMENTS

| EP | 0 380 666 | 8/1990 |
|---|---|---|
| EP | 0 466 518 | 1/1992 |

(Continued)

*Primary Examiner* — David Isabella
*Assistant Examiner* — Suba Ganesan
(74) *Attorney, Agent, or Firm* — Vidas, Arrett & Steinkraus, P.A.

(57) ABSTRACT

A cardiac valve with a first anchor frame and a cover on the first anchor frame for unidirectional flow of a liquid through the valve.

13 Claims, 14 Drawing Sheets

(56) References Cited

U.S. PATENT DOCUMENTS

| | | | |
|---|---|---|---|
| 5,741,326 A | 4/1998 | Solovay | 623/1 |
| 5,741,333 A | 4/1998 | Frid | 623/12 |
| 5,800,506 A | 9/1998 | Perouse | 623/1 |
| 5,824,061 A | 10/1998 | Quijano et al. | 623/2 |
| 5,843,167 A * | 12/1998 | Dwyer et al. | 623/1.14 |
| 5,855,601 A * | 1/1999 | Bessler et al. | 623/2.38 |
| 5,879,320 A | 3/1999 | Cazenave | 604/8 |
| 5,895,419 A | 4/1999 | Tweden et al. | 623/2 |
| 5,910,170 A | 6/1999 | Reimink et al. | 623/2 |
| 6,010,531 A | 1/2000 | Donlon et al. | 623/2 |
| 6,042,607 A | 3/2000 | Williamson, IV et al. | 623/2 |
| 6,139,575 A | 10/2000 | Shu et al. | 623/2.12 |
| 6,287,334 B1 | 9/2001 | Moll et al. | 623/1.24 |
| 6,312,447 B1 | 11/2001 | Grimes | 606/219 |
| 6,355,030 B1 | 3/2002 | Aldrich et al. | 606/28 |
| 6,402,780 B2 | 6/2002 | Williamson, IV et al. | 623/2 |
| 6,419,696 B1 | 7/2002 | Ortiz et al. | 623/2.37 |
| 6,425,916 B1 | 7/2002 | Garrison et al. | 623/2.11 |
| 6,440,164 B1 | 8/2002 | DiMatteo et al. | 623/1.24 |
| 6,451,054 B1 | 9/2002 | Stevens | 623/2.11 |
| 6,454,799 B1 | 9/2002 | Schreck | 623/2.18 |
| 6,461,366 B1 | 10/2002 | Seguin | 606/144 |
| 6,503,272 B2 | 1/2003 | Duerig et al. | 623/1.24 |
| 6,508,833 B2 | 1/2003 | Pavcnik et al. | 623/1.15 |
| 6,564,805 B2 | 5/2003 | Garrison et al. | 128/898 |
| 6,569,196 B1 | 5/2003 | Vesely | 623/2.14 |
| 6,602,286 B1 | 8/2003 | Strecker | 623/1.24 |
| 6,629,534 B1 | 10/2003 | St. Goar et al. | 128/898 |
| 6,635,085 B1 | 10/2003 | Caffey et al. | 623/2.1 |
| 6,666,885 B2 | 12/2003 | Moe | 623/2.36 |
| 6,666,886 B1 | 12/2003 | Tranquillo et al. | 623/2.42 |
| 6,669,725 B2 | 12/2003 | Scott | 623/2.36 |
| 6,673,109 B2 | 1/2004 | Cox | 623/2.12 |
| 6,676,698 B2 | 1/2004 | McGuckin, Jr. et al. | 623/1.24 |
| 6,676,702 B2 | 1/2004 | Mathis | 623/2.36 |
| 6,682,558 B2 | 1/2004 | Tu et al. | 623/2.11 |
| 6,682,559 B2 | 1/2004 | Myers et al. | 623/2.13 |
| 6,685,739 B2 | 2/2004 | DiMatteo et al. | 623/1.24 |
| 6,692,512 B2 | 2/2004 | Jang | 606/200 |
| 6,695,866 B1 | 2/2004 | Kuehn et al. | 606/213 |
| 6,695,878 B2 | 2/2004 | McGuckin, Jr. et al. | 623/1.19 |
| 6,709,456 B2 | 3/2004 | Langberg et al. | 623/2.37 |
| 6,709,457 B1 | 3/2004 | Otte et al. | 623/2.4 |
| 6,716,241 B2 | 4/2004 | Wilder et al. | 623/1.24 |
| 6,716,244 B2 | 4/2004 | Klaco | 623/2.4 |
| 6,719,767 B1 | 4/2004 | Kimblad | 606/151 |
| 6,719,784 B2 | 4/2004 | Henderson | 623/1.44 |
| 6,719,786 B2 | 4/2004 | Ryan et al. | 623/2.11 |
| 6,719,787 B2 | 4/2004 | Cox | 623/2.12 |
| 6,719,788 B2 | 4/2004 | Cox | 623/2.12 |
| 6,719,789 B2 | 4/2004 | Cox | 623/2.13 |
| 6,719,790 B2 | 4/2004 | Brendzel et al. | 623/2.4 |
| 6,723,038 B1 | 4/2004 | Schroeder et al. | 600/16 |
| 6,723,122 B2 | 4/2004 | Yang et al. | 623/2.1 |
| 6,723,123 B1 | 4/2004 | Kazatchkov et al. | 623/2.2 |
| 6,726,715 B2 | 4/2004 | Sutherland | 623/2.1 |
| 6,726,716 B2 | 4/2004 | Marquez | 623/2.36 |
| 6,726,717 B2 | 4/2004 | Alfieri et al. | 623/2.36 |
| 6,730,118 B2 | 5/2004 | Spenser et al. | 623/1.24 |
| 6,730,121 B2 | 5/2004 | Ortiz et al. | 623/2.17 |
| 6,730,122 B1 | 5/2004 | Pan et al. | 623/2.33 |
| 6,736,845 B2 | 5/2004 | Marquez et al. | 623/2.11 |
| 6,736,846 B2 | 5/2004 | Cox | 623/2.12 |
| 6,749,630 B2 | 6/2004 | McCarthy et al. | 623/2.36 |
| 6,752,813 B2 | 6/2004 | Goldfarb et al. | 606/139 |
| 6,752,828 B2 | 6/2004 | Thornton | 623/1.24 |
| 6,755,857 B2 | 6/2004 | Peterson et al. | 623/2.17 |
| 6,761,734 B2 | 7/2004 | Suhr | 623/1.35 |
| 6,761,735 B2 | 7/2004 | Eberhardt et al. | 623/2.1 |
| 6,764,494 B2 | 7/2004 | Menz et al. | 606/159 |
| 6,764,508 B1 | 7/2004 | Roehe et al. | 623/2.11 |
| 6,764,509 B2 | 7/2004 | Chinn et al. | 623/2.12 |
| 6,764,510 B2 | 7/2004 | Vidlund et al. | 623/2.34 |
| 6,767,362 B2 | 7/2004 | Schreck | 623/2.11 |
| 6,769,434 B2 | 8/2004 | Liddicoat et al. | 128/898 |
| 6,770,083 B2 | 8/2004 | Seguin | 606/142 |
| 6,780,200 B2 | 8/2004 | Jansen | 623/2.17 |
| 6,786,924 B2 | 9/2004 | Ryan et al. | 623/2.36 |
| 6,786,925 B1 | 9/2004 | Schoon et al. | 623/2.38 |
| 6,790,229 B1 | 9/2004 | Berreklouw | 623/2.1 |
| 6,790,230 B2 | 9/2004 | Beyersdorf et al. | 623/2.18 |
| 6,790,231 B2 | 9/2004 | Liddicoat et al. | 623/2.37 |
| 6,793,673 B2 | 9/2004 | Kowalsky et al. | 623/2.36 |
| 6,797,000 B2 | 9/2004 | Simpson et al. | 623/2.15 |
| 6,797,001 B2 | 9/2004 | Mathis et al. | 623/2.37 |
| 6,797,002 B2 | 9/2004 | Spence et al. | 623/2.38 |
| 6,802,860 B2 | 10/2004 | Cosgrove et al. | 623/2.11 |
| 6,805,710 B2 | 10/2004 | Bolling et al. | 623/2.36 |
| 6,805,711 B2 | 10/2004 | Quijano et al. | 623/2.37 |
| 6,810,882 B2 | 11/2004 | Langberg et al. | 128/898 |
| 6,821,297 B2 | 11/2004 | Snyders | 623/2.18 |
| 6,824,562 B2 | 11/2004 | Mathis et al. | 623/2.36 |
| 6,830,584 B1 | 12/2004 | Seguin | 623/2.11 |
| 6,830,585 B1 | 12/2004 | Artof et al. | 623/2.11 |
| 6,837,902 B2 | 1/2005 | Nguyen et al. | 623/2.13 |
| 6,840,246 B2 | 1/2005 | Downing | 128/898 |
| 6,840,957 B2 | 1/2005 | DiMatteo et al. | 623/1.24 |
| 6,846,324 B2 | 1/2005 | Stobie | 623/2.11 |
| 6,846,325 B2 | 1/2005 | Liddicoat | 623/2.4 |
| 6,858,039 B2 | 2/2005 | McCarthy | 623/2.36 |
| 6,869,444 B2 | 3/2005 | Gabbay | 623/2.36 |
| 6,872,226 B2 | 3/2005 | Cali et al. | 623/2.13 |
| 6,875,224 B2 | 4/2005 | Grimes | 606/219 |
| 6,875,230 B1 | 4/2005 | Morita et al. | 623/2.12 |
| 6,875,231 B2 | 4/2005 | Anduiza et al. | 623/2.14 |
| 6,881,199 B2 | 4/2005 | Wilk et al. | 604/9 |
| 6,881,224 B2 | 4/2005 | Kruse et al. | 623/2.11 |
| 6,883,522 B2 | 4/2005 | Spence et al. | 128/898 |
| 6,890,352 B1 | 5/2005 | Lentell | 623/2.27 |
| 6,890,353 B2 | 5/2005 | Cohn et al. | 623/2.37 |
| 6,893,459 B1 | 5/2005 | Macoviak | 623/2.11 |
| 6,893,460 B2 | 5/2005 | Spenser et al. | 623/2.14 |
| 6,896,700 B2 | 5/2005 | Lu et al. | 623/2.34 |
| 6,902,576 B2 | 6/2005 | Drasler et al. | 623/1.24 |
| 6,908,478 B2 | 6/2005 | Alferness et al. | 623/1.11 |
| 6,908,481 B2 | 6/2005 | Cribier | 623/2.11 |
| 6,911,043 B2 | 6/2005 | Myers et al. | 623/2.13 |
| 6,913,608 B2 | 7/2005 | Liddicoat et al. | 606/151 |
| 6,916,338 B2 | 7/2005 | Speziali | 623/2.12 |
| 6,918,917 B1 | 7/2005 | Nguyen et al. | 606/139 |
| 6,921,407 B2 | 7/2005 | Nguyen et al. | 606/142 |
| 6,921,811 B2 | 7/2005 | Zamora et al. | 536/21 |
| 6,926,715 B1 | 8/2005 | Hauck et al. | 606/41 |
| 6,926,730 B1 | 8/2005 | Nguyen et al. | 606/213 |
| 6,929,653 B2 | 8/2005 | Strecter | 606/200 |
| 6,932,838 B2 | 8/2005 | Schwartz et al. | 623/1.23 |
| 6,936,067 B2 | 8/2005 | Buchanan | 623/2.28 |
| 6,939,359 B2 | 9/2005 | Tu et al. | 606/159 |
| 6,942,694 B2 | 9/2005 | Liddicoat et al. | 623/2.36 |
| 6,945,957 B2 | 9/2005 | Freyman | 604/96.01 |
| 6,945,978 B1 | 9/2005 | Hyde | 606/142 |
| 6,945,996 B2 | 9/2005 | Sedransk | 623/2.12 |
| 6,945,997 B2 | 9/2005 | Huynh et al. | 623/2.17 |
| 6,949,122 B2 | 9/2005 | Adams et al. | 623/2.36 |
| 6,951,571 B1 | 10/2005 | Srivastava | 623/1.24 |
| 6,951,573 B1 | 10/2005 | Dilling | 623/2.2 |
| 6,955,689 B2 | 10/2005 | Ryan et al. | 623/2.36 |
| 6,958,076 B2 | 10/2005 | Acosta et al. | 623/1.24 |
| 6,962,605 B2 | 11/2005 | Cosgrove et al. | 623/2.36 |
| 6,964,682 B2 | 11/2005 | Nguyen-Thien-Nhon et al. | 623/2.11 |
| 6,964,683 B2 | 11/2005 | Kowalsky et al. | 623/2.36 |
| 6,964,684 B2 | 11/2005 | Ortiz et al. | 623/2.37 |
| 6,966,925 B2 | 11/2005 | Stobie | 623/2.11 |
| 6,966,926 B2 | 11/2005 | Mathis | 623/2.36 |
| 6,974,464 B2 | 12/2005 | Quijano et al. | 606/108 |
| 6,974,474 B2 | 12/2005 | Pavcnik et al. | 623/1.24 |
| 6,974,476 B2 | 12/2005 | McGuckin, Jr. et al. | 623/2.36 |
| 6,976,995 B2 | 12/2005 | Mathis et al. | 623/2.37 |
| 6,979,350 B2 | 12/2005 | Moll et al. | 623/1.24 |
| 6,986,775 B2 | 1/2006 | Morales et al. | 606/139 |
| 6,989,027 B2 | 1/2006 | Allen et al. | 623/2.18 |
| 6,989,028 B2 | 1/2006 | Lashinski et al. | 623/2.37 |
| 6,997,950 B2 | 2/2006 | Chawla | 623/2.1 |

| | | | |
|---|---|---|---|
| 6,997,951 B2 | 2/2006 | Solem et al. | 623/2.37 |
| 7,004,176 B2 | 2/2006 | Lau | 128/898 |
| 7,007,396 B2 | 3/2006 | Rudko et al. | 33/512 |
| 7,011,669 B2 | 3/2006 | Kimblad | 606/151 |
| 7,011,681 B2 | 3/2006 | Vesely | 623/2.11 |
| 7,011,682 B2 | 3/2006 | Lashinski et al. | 623/2.37 |
| 7,018,406 B2 | 3/2006 | Seguin et al. | 623/2.1 |
| 7,018,407 B1 | 3/2006 | Wright et al. | 623/2.11 |
| 7,018,408 B2 | 3/2006 | Bailey et al. | 623/2.11 |
| 7,022,134 B1 | 4/2006 | Quijano et al. | 623/1.24 |
| 7,025,780 B2 | 4/2006 | Gabbay | 623/2.13 |
| 7,033,390 B2 | 4/2006 | Johnson et al. | 623/2.11 |
| 7,037,333 B2 | 5/2006 | Myers et al. | 623/2.13 |
| 7,037,334 B1 | 5/2006 | Hlavka et al. | 623/2.36 |
| 7,041,128 B2 | 5/2006 | McGuckin, Jr. et al. | 623/1.36 |
| 7,041,132 B2 | 5/2006 | Quijano et al. | 623/2.11 |
| 7,044,966 B2 | 5/2006 | Svanidze et al. | 623/2.1 |
| 7,044,967 B1 | 5/2006 | Solem et al. | 623/2.36 |
| 7,048,754 B2 | 5/2006 | Martin et al. | 606/232 |
| 7,048,757 B2 | 5/2006 | Shaknovich | 623/1.24 |
| 7,052,487 B2 | 5/2006 | Cohn et al. | 604/509 |
| 7,052,507 B2 | 5/2006 | Wakuda et al. | 606/194 |
| 7,063,722 B2 | 6/2006 | Marquez | 623/2.36 |
| 7,066,954 B2 | 6/2006 | Ryan et al. | 623/2.36 |
| 7,070,616 B2 | 7/2006 | Majercak et al. | 623/1.24 |
| 7,077,862 B2 | 7/2006 | Vidlund et al. | 623/2.36 |
| 7,081,131 B2 | 7/2006 | Thornton | 623/1.24 |
| 7,087,064 B1 | 8/2006 | Hyde | 606/142 |
| 7,089,051 B2 | 8/2006 | Jäverud et al. | 600/547 |
| 7,090,695 B2 | 8/2006 | Solem et al. | 623/2.37 |
| 2001/0002445 A1* | 5/2001 | Vesely | 623/2.11 |
| 2002/0013571 A1 | 1/2002 | Goldfarb et al. | 606/1 |
| 2002/0026216 A1 | 2/2002 | Grimes | 606/213 |
| 2002/0032481 A1* | 3/2002 | Gabbay | 623/2.11 |
| 2002/0082630 A1 | 6/2002 | Menz et al. | 606/167 |
| 2002/0123802 A1 | 9/2002 | Snyders | 623/2.18 |
| 2002/0151970 A1 | 10/2002 | Garrison et al. | 623/2.11 |
| 2002/0183835 A1 | 12/2002 | Taylor et al. | 623/2.11 |
| 2002/0183838 A1 | 12/2002 | Liddicoat et al. | 623/2.11 |
| 2002/0198594 A1 | 12/2002 | Schreck | 623/2.11 |
| 2003/0050694 A1 | 3/2003 | Yang et al. | 623/2.11 |
| 2003/0130729 A1 | 7/2003 | Paniagua et al. | 623/2.11 |
| 2003/0163194 A1 | 8/2003 | Quijano et al. | 623/2.11 |
| 2003/0167071 A1 | 9/2003 | Martin et al. | 606/232 |
| 2003/0171806 A1 | 9/2003 | Mathis et al. | 623/2.36 |
| 2003/0199975 A1 | 10/2003 | Gabbay | 623/2.36 |
| 2003/0229394 A1 | 12/2003 | Ogle et al. | 623/2.14 |
| 2003/0229395 A1 | 12/2003 | Cox | 623/2.36 |
| 2003/0233142 A1 | 12/2003 | Morales et al. | 623/2.37 |
| 2003/0236568 A1 | 12/2003 | Hojeibane et al. | 623/1.24 |
| 2003/0236569 A1 | 12/2003 | Mathis et al. | 623/1.26 |
| 2004/0002719 A1 | 1/2004 | Oz et al. | 606/142 |
| 2004/0003819 A1 | 1/2004 | St. Goar et al. | 128/898 |
| 2004/0010305 A1 | 1/2004 | Alferness et al. | 623/1.11 |
| 2004/0015230 A1 | 1/2004 | Moll et al. | 623/1.24 |
| 2004/0015232 A1 | 1/2004 | Shu et al. | 623/2.4 |
| 2004/0015233 A1 | 1/2004 | Jansen | 623/2.18 |
| 2004/0019374 A1 | 1/2004 | Hojeibane et al. | 623/1.13 |
| 2004/0019377 A1 | 1/2004 | Taylor et al. | 623/2.11 |
| 2004/0019378 A1 | 1/2004 | Hlavka et al. | 623/2.11 |
| 2004/0024447 A1 | 2/2004 | Haverich | 623/1.24 |
| 2004/0024451 A1 | 2/2004 | Johnson et al. | 623/2.11 |
| 2004/0024452 A1 | 2/2004 | Kruse et al. | 623/2.13 |
| 2004/0030321 A1 | 2/2004 | Fangrow, Jr. | 604/533 |
| 2004/0030381 A1 | 2/2004 | Shu | 623/2.11 |
| 2004/0030382 A1 | 2/2004 | St. Goar et al. | 623/2.36 |
| 2004/0030405 A1 | 2/2004 | Carpentier et al. | 623/23.72 |
| 2004/0034380 A1 | 2/2004 | Woolfson et al. | 606/170 |
| 2004/0034411 A1 | 2/2004 | Quijano et al. | 623/2.11 |
| 2004/0039436 A1 | 2/2004 | Spenser et al. | 623/1.13 |
| 2004/0039442 A1 | 2/2004 | St. Goar et al. | 623/2.36 |
| 2004/0039443 A1 | 2/2004 | Solem et al. | 623/2.37 |
| 2004/0044350 A1 | 3/2004 | Martin et al. | 606/139 |
| 2004/0044365 A1 | 3/2004 | Bachman | 606/213 |
| 2004/0044403 A1 | 3/2004 | Bischoff et al. | 623/1.41 |
| 2004/0049207 A1 | 3/2004 | Goldfarb et al. | 606/139 |
| 2004/0049211 A1 | 3/2004 | Tremulis et al. | 606/153 |
| 2004/0049266 A1 | 3/2004 | Anduiza et al. | 623/2.11 |
| 2004/0059351 A1 | 3/2004 | Eigler et al. | 606/148 |
| 2004/0059411 A1 | 3/2004 | Strecker | 623/1.23 |
| 2004/0059412 A1 | 3/2004 | Lytle, IV et al. | 623/2.11 |
| 2004/0060161 A1 | 4/2004 | Leal et al. | 29/558 |
| 2004/0073301 A1 | 4/2004 | Donlon et al. | 623/2.11 |
| 2004/0073302 A1 | 4/2004 | Rourke et al. | 623/2.36 |
| 2004/0078072 A1 | 4/2004 | Tu et al. | 623/1.23 |
| 2004/0078074 A1 | 4/2004 | Anderson et al. | 623/2.11 |
| 2004/0082910 A1 | 4/2004 | Constantz et al. | 604/101.04 |
| 2004/0082923 A1 | 4/2004 | Field | 604/267 |
| 2004/0082991 A1 | 4/2004 | Nguyen et al. | 623/2.14 |
| 2004/0087975 A1 | 5/2004 | Lucatero et al. | 606/139 |
| 2004/0088045 A1 | 5/2004 | Cox | 623/2.13 |
| 2004/0088046 A1 | 5/2004 | Speziali | 623/2.19 |
| 2004/0092858 A1 | 5/2004 | Wilson et al. | 604/9 |
| 2004/0093060 A1 | 5/2004 | Seguin et al. | 623/1.11 |
| 2004/0093070 A1 | 5/2004 | Hojeibane et al. | 623/1.15 |
| 2004/0093080 A1 | 5/2004 | Helmus et al. | 623/2.41 |
| 2004/0097979 A1 | 5/2004 | Svanidze et al. | 606/151 |
| 2004/0098098 A1 | 5/2004 | McGuckin, Jr. et al. | 623/1.14 |
| 2004/0098112 A1 | 5/2004 | DiMatteo et al. | 623/1.24 |
| 2004/0102839 A1 | 5/2004 | Cohn et al. | 623/2.11 |
| 2004/0102840 A1 | 5/2004 | Solem et al. | 623/2.11 |
| 2004/0102842 A1 | 5/2004 | Jansen | 623/2.38 |
| 2004/0106976 A1 | 6/2004 | Bailey et al. | 623/1.11 |
| 2004/0106990 A1 | 6/2004 | Spence et al. | 623/2.11 |
| 2004/0106991 A1 | 6/2004 | Hopkins et al. | 623/2.13 |
| 2004/0111096 A1 | 6/2004 | Tu et al. | 606/108 |
| 2004/0117009 A1 | 6/2004 | Cali et al. | 623/2.12 |
| 2004/0122448 A1 | 6/2004 | Levine | 606/139 |
| 2004/0122512 A1 | 6/2004 | Navia et al. | 623/2.12 |
| 2004/0122513 A1 | 6/2004 | Navia et al. | 623/2.12 |
| 2004/0122514 A1 | 6/2004 | Fogarty et al. | 623/2.14 |
| 2004/0122515 A1 | 6/2004 | Chu | 623/2.29 |
| 2004/0122516 A1 | 6/2004 | Fogarty et al. | 623/2.37 |
| 2004/0127979 A1 | 7/2004 | Wilson et al. | 623/2.1 |
| 2004/0127980 A1 | 7/2004 | Kowalsky et al. | 623/2.11 |
| 2004/0127981 A1 | 7/2004 | Rahdert et al. | 623/2.36 |
| 2004/0127982 A1 | 7/2004 | Machold et al. | 623/2.36 |
| 2004/0133220 A1 | 7/2004 | Lashinski et al. | 606/151 |
| 2004/0133267 A1 | 7/2004 | Lane | 623/1.24 |
| 2004/0133273 A1 | 7/2004 | Cox | 623/2.11 |
| 2004/0138742 A1 | 7/2004 | Myers et al. | 623/2.12 |
| 2004/0138743 A1 | 7/2004 | Myers et al. | 623/2.13 |
| 2004/0138744 A1 | 7/2004 | Lashinski et al. | 623/2.36 |
| 2004/0138745 A1 | 7/2004 | Macoviak et al. | 623/2.36 |
| 2004/0148018 A1 | 7/2004 | Carpentier et al. | 623/2.18 |
| 2004/0148019 A1 | 7/2004 | Vidlund et al. | 623/2.36 |
| 2004/0148020 A1 | 7/2004 | Vidlund et al. | 623/2.36 |
| 2004/0153052 A1 | 8/2004 | Mathis | 606/1 |
| 2004/0153146 A1 | 8/2004 | Lashinski et al. | 623/2.36 |
| 2004/0153147 A1 | 8/2004 | Mathis | 623/2.37 |
| 2004/0158321 A1 | 8/2004 | Reuter et al. | 623/2.36 |
| 2004/0162610 A1 | 8/2004 | Liska et al. | 623/2.11 |
| 2004/0167539 A1 | 8/2004 | Kuehn et al. | 606/108 |
| 2004/0167620 A1 | 8/2004 | Ortiz et al. | 623/2.11 |
| 2004/0172046 A1 | 9/2004 | Hlavka et al. | 606/142 |
| 2004/0176839 A1 | 9/2004 | Huynh et al. | 623/2.4 |
| 2004/0176840 A1 | 9/2004 | Langberg et al. | 623/2.37 |
| 2004/0181238 A1 | 9/2004 | Zarbatany et al. | 606/108 |
| 2004/0186444 A1 | 9/2004 | Daly et al. | 604/247 |
| 2004/0186558 A1 | 9/2004 | Pavcnik et al. | 623/1.24 |
| 2004/0186561 A1 | 9/2004 | McGuckin, Jr. et al. | 623/1.36 |
| 2004/0186563 A1 | 9/2004 | Lobbi | 623/2.11 |
| 2004/0186565 A1 | 9/2004 | Schreck | 623/2.18 |
| 2004/0186566 A1 | 9/2004 | Hindrichs et al. | 623/2.37 |
| 2004/0193191 A1 | 9/2004 | Starksen et al. | 606/153 |
| 2004/0193253 A1 | 9/2004 | Thorpe et al. | 623/1.24 |
| 2004/0193260 A1 | 9/2004 | Alferness et al. | 623/2.11 |
| 2004/0199155 A1 | 10/2004 | Mollenauer | 606/27 |
| 2004/0199183 A1 | 10/2004 | Oz et al. | 606/142 |
| 2004/0199191 A1 | 10/2004 | Schwartz | 606/159 |
| 2004/0204758 A1 | 10/2004 | Eberhardt et al. | 623/2.15 |
| 2004/0206363 A1 | 10/2004 | McCarthy et al. | 128/898 |
| 2004/0210240 A1 | 10/2004 | Saint | 606/139 |
| 2004/0210301 A1 | 10/2004 | Obermiller | 623/1.24 |
| 2004/0210303 A1 | 10/2004 | Sedransk | 623/2.1 |
| 2004/0210304 A1 | 10/2004 | Seguin et al. | 623/2.11 |
| 2004/0210305 A1 | 10/2004 | Shu et al. | 623/2.11 |
| 2004/0210306 A1 | 10/2004 | Quijano et al. | 623/2.17 |

| Publication No. | Date | Inventor | Class |
|---|---|---|---|
| 2004/0210307 A1 | 10/2004 | Khairkhahan | 623/2.18 |
| 2004/0215333 A1 | 10/2004 | Duran et al. | 623/1.24 |
| 2004/0215339 A1 | 10/2004 | Drasler et al. | 623/3.1 |
| 2004/0220654 A1 | 11/2004 | Mathis et al. | 623/1.11 |
| 2004/0220657 A1 | 11/2004 | Nieminen et al. | 623/1.15 |
| 2004/0225322 A1 | 11/2004 | Garrison et al. | 606/200 |
| 2004/0225344 A1 | 11/2004 | Hoffa et al. | 623/1.1 |
| 2004/0225348 A1 | 11/2004 | Case et al. | 623/1.15 |
| 2004/0225352 A1 | 11/2004 | Osborne et al. | 623/1.24 |
| 2004/0225353 A1 | 11/2004 | McGuckin, Jr. et al. | 623/2.11 |
| 2004/0225354 A1 | 11/2004 | Allen et al. | 623/2.11 |
| 2004/0225355 A1 | 11/2004 | Stevens | 623/2.11 |
| 2004/0225356 A1 | 11/2004 | Frater | 623/2.14 |
| 2004/0230117 A1 | 11/2004 | Tosaya et al. | 600/439 |
| 2004/0230297 A1 | 11/2004 | Thornton | 623/1.24 |
| 2004/0236411 A1 | 11/2004 | Sarac et al. | 623/1.26 |
| 2004/0236418 A1 | 11/2004 | Stevens | 623/2.11 |
| 2004/0236419 A1 | 11/2004 | Milo | 623/2.36 |
| 2004/0243153 A1 | 12/2004 | Liddicoat et al. | 606/151 |
| 2004/0243219 A1 | 12/2004 | Fischer et al. | 623/1.15 |
| 2004/0243227 A1 | 12/2004 | Starksen et al. | 623/2.11 |
| 2004/0243228 A1 | 12/2004 | Kowalsky et al. | 623/2.11 |
| 2004/0243230 A1 | 12/2004 | Navia et al. | 623/2.36 |
| 2004/0254600 A1 | 12/2004 | Zarbatany et al. | 606/194 |
| 2004/0254636 A1 | 12/2004 | Flagle et al. | 623/1.24 |
| 2004/0260276 A1 | 12/2004 | Rudko et al. | 606/15 |
| 2004/0260317 A1 | 12/2004 | Bloom et al. | 606/151 |
| 2004/0260322 A1 | 12/2004 | Rudko et al. | 606/167 |
| 2004/0260389 A1 | 12/2004 | Case et al. | 623/1.24 |
| 2004/0260390 A1 | 12/2004 | Sarac et al. | 623/1.24 |
| 2004/0260393 A1 | 12/2004 | Rahdert et al. | 623/2.36 |
| 2004/0260394 A1 | 12/2004 | Douk et al. | 623/2.36 |
| 2004/0267357 A1 | 12/2004 | Allen et al. | 623/2.11 |
| 2005/0004583 A1 | 1/2005 | Oz et al. | 606/142 |
| 2005/0004667 A1 | 1/2005 | Swinford et al. | 623/2.36 |
| 2005/0010285 A1 | 1/2005 | Lambrecht et al. | 623/2.18 |
| 2005/0010287 A1 | 1/2005 | Macoviak et al. | 623/2.36 |
| 2005/0015112 A1 | 1/2005 | Cohn et al. | 606/200 |
| 2005/0021056 A1 | 1/2005 | St. Goar et al. | 606/144 |
| 2005/0021136 A1 | 1/2005 | Xie et al. | 623/2.14 |
| 2005/0027261 A1 | 2/2005 | Weaver et al. | 604/246 |
| 2005/0027348 A1 | 2/2005 | Case et al. | 623/1.24 |
| 2005/0027351 A1 | 2/2005 | Reuter et al. | 623/2.11 |
| 2005/0027353 A1 | 2/2005 | Alferness et al. | 623/2.11 |
| 2005/0033398 A1 | 2/2005 | Seguin | 623/1.11 |
| 2005/0033419 A1 | 2/2005 | Alferness et al. | 623/2.11 |
| 2005/0033446 A1 | 2/2005 | Deem et al. | 623/23.6 |
| 2005/0038506 A1 | 2/2005 | Webler et al. | 623/2.11 |
| 2005/0038507 A1 | 2/2005 | Alferness et al. | 623/2.11 |
| 2005/0043790 A1 | 2/2005 | Seguin | 623/2.18 |
| 2005/0043792 A1 | 2/2005 | Solem et al. | 623/2.36 |
| 2005/0049679 A1 | 3/2005 | Taylor et al. | 623/1.15 |
| 2005/0049692 A1 | 3/2005 | Numamoto et al. | 623/1.24 |
| 2005/0049696 A1 | 3/2005 | Siess et al. | 623/2.11 |
| 2005/0049697 A1 | 3/2005 | Sievers | 623/2.26 |
| 2005/0054977 A1 | 3/2005 | Laird et al. | 604/96.01 |
| 2005/0055079 A1 | 3/2005 | Duran | 623/1.13 |
| 2005/0055087 A1 | 3/2005 | Starksen | 623/2.11 |
| 2005/0055088 A1 | 3/2005 | Liddicoat et al. | 623/2.11 |
| 2005/0055089 A1 | 3/2005 | Macoviak et al. | 623/2.37 |
| 2005/0060029 A1 | 3/2005 | Le et al. | 623/2.11 |
| 2005/0060030 A1 | 3/2005 | Lashinski et al. | 623/2.37 |
| 2005/0065460 A1 | 3/2005 | Laird | 604/20 |
| 2005/0065550 A1 | 3/2005 | Starksen et al. | 606/219 |
| 2005/0065594 A1 | 3/2005 | Dimatteo et al. | 623/1.24 |
| 2005/0065597 A1 | 3/2005 | Lansac | 623/2.11 |
| 2005/0070998 A1 | 3/2005 | Rourke et al. | 623/2.11 |
| 2005/0075584 A1 | 4/2005 | Cali | 600/587 |
| 2005/0075659 A1 | 4/2005 | Realyvasquez et al. | 606/167 |
| 2005/0075662 A1 | 4/2005 | Pedersen et al. | 606/194 |
| 2005/0075712 A1 | 4/2005 | Biancucci et al. | 623/1.11 |
| 2005/0075713 A1 | 4/2005 | Biancucci et al. | 623/1.11 |
| 2005/0075717 A1 | 4/2005 | Nguyen et al. | 623/1.26 |
| 2005/0075718 A1 | 4/2005 | Nguyen et al. | 623/1.26 |
| 2005/0075719 A1 | 4/2005 | Bergheim | 623/1.26 |
| 2005/0075720 A1 | 4/2005 | Nguyen et al. | 623/1.26 |
| 2005/0075723 A1 | 4/2005 | Schroeder et al. | 623/2.1 |
| 2005/0075724 A1 | 4/2005 | Svanidze et al. | 623/2.11 |
| 2005/0075725 A1 | 4/2005 | Rowe | 623/2.14 |
| 2005/0075726 A1 | 4/2005 | Svanidze et al. | 623/2.14 |
| 2005/0075729 A1 | 4/2005 | Nguyen et al. | 623/2.18 |
| 2005/0075730 A1 | 4/2005 | Myers et al. | 623/2.18 |
| 2005/0075731 A1 | 4/2005 | Artof et al. | 623/2.18 |
| 2005/0080483 A1 | 4/2005 | Solem et al. | 623/2.11 |
| 2005/0085900 A1 | 4/2005 | Case et al. | 623/1.24 |
| 2005/0085903 A1 | 4/2005 | Lau | 623/2.11 |
| 2005/0085904 A1 | 4/2005 | Lemmon | 623/2.11 |
| 2005/0090846 A1 | 4/2005 | Pedersen et al. | 606/159 |
| 2005/0096735 A1 | 5/2005 | Hojeibane et al. | 623/1.24 |
| 2005/0096738 A1 | 5/2005 | Cali et al. | 623/2.18 |
| 2005/0096739 A1 | 5/2005 | Cao | 623/2.19 |
| 2005/0096740 A1 | 5/2005 | Langberg et al. | 623/2.36 |
| 2005/0101975 A1 | 5/2005 | Nguyen et al. | 606/151 |
| 2005/0102026 A1 | 5/2005 | Turner et al. | 623/2.1 |
| 2005/0107810 A1 | 5/2005 | Morales et al. | 606/143 |
| 2005/0107811 A1 | 5/2005 | Starksen et al. | 606/143 |
| 2005/0107812 A1 | 5/2005 | Starksen et al. | 606/143 |
| 2005/0107872 A1 | 5/2005 | Mensah et al. | 623/2.14 |
| 2005/0113910 A1 | 5/2005 | Paniagua et al. | 623/2.14 |
| 2005/0119673 A1 | 6/2005 | Gordon et al. | 606/151 |
| 2005/0119734 A1 | 6/2005 | Spence et al. | 623/2.11 |
| 2005/0119735 A1 | 6/2005 | Spence et al. | 623/2.36 |
| 2005/0125011 A1 | 6/2005 | Spence et al. | 606/144 |
| 2005/0131438 A1 | 6/2005 | Cohn | 606/170 |
| 2005/0137449 A1 | 6/2005 | Nieminen et al. | 600/37 |
| 2005/0137450 A1 | 6/2005 | Aronson et al. | 600/37 |
| 2005/0137451 A1 | 6/2005 | Gordon et al. | 600/37 |
| 2005/0137676 A1 | 6/2005 | Richardson et al. | 623/1.11 |
| 2005/0137681 A1 | 6/2005 | Shoemaker et al. | 623/1.23 |
| 2005/0137682 A1 | 6/2005 | Justino | 623/1.24 |
| 2005/0137685 A1 | 6/2005 | Nieminen et al. | 623/2.11 |
| 2005/0137686 A1* | 6/2005 | Salahieh et al. | 623/2.11 |
| 2005/0137688 A1 | 6/2005 | Salahieh et al. | 623/2.11 |
| 2005/0137689 A1 | 6/2005 | Salahieh et al. | 623/2.11 |
| 2005/0137690 A1 | 6/2005 | Salahieh et al. | 623/2.11 |
| 2005/0137691 A1 | 6/2005 | Salahieh et al. | 623/2.11 |
| 2005/0137692 A1 | 6/2005 | Haug et al. | 623/2.11 |
| 2005/0137693 A1 | 6/2005 | Haug et al. | 623/2.11 |
| 2005/0137694 A1 | 6/2005 | Haug et al. | 623/2.11 |
| 2005/0137696 A1 | 6/2005 | Salahieh et al. | 623/2.11 |
| 2005/0137697 A1 | 6/2005 | Salahieh et al. | 623/2.11 |
| 2005/0137698 A1 | 6/2005 | Salahieh et al. | 623/2.11 |
| 2005/0137699 A1 | 6/2005 | Salahieh et al. | 623/2.11 |
| 2005/0137700 A1 | 6/2005 | Spence et al. | 623/2.36 |
| 2005/0137701 A1 | 6/2005 | Salahieh et al. | 623/2.38 |
| 2005/0137702 A1 | 6/2005 | Haug et al. | 623/2.38 |
| 2005/0143807 A1 | 6/2005 | Pavcnik et al. | 623/1.24 |
| 2005/0143809 A1 | 6/2005 | Salahieh et al. | 623/2.11 |
| 2005/0143810 A1 | 6/2005 | Dauner et al. | 623/2.12 |
| 2005/0143811 A1 | 6/2005 | Realyvasquez | 623/2.36 |
| 2005/0149014 A1 | 7/2005 | Hauck et al. | 606/41 |
| 2005/0149179 A1 | 7/2005 | Mathis et al. | 623/2.11 |
| 2005/0149180 A1 | 7/2005 | Mathis et al. | 623/2.11 |
| 2005/0149181 A1 | 7/2005 | Eberhardt | 623/2.14 |
| 2005/0159810 A1 | 7/2005 | Filsoufi | 623/2.1 |
| 2005/0159811 A1 | 7/2005 | Lane | 623/2.14 |
| 2005/0165477 A1 | 7/2005 | Anduiza et al. | 623/2.11 |
| 2005/0165478 A1 | 7/2005 | Song | 623/2.22 |
| 2005/0171472 A1 | 8/2005 | Lutter | 604/101.03 |
| 2005/0171601 A1 | 8/2005 | Cosgrove et al. | 623/2.11 |
| 2005/0177227 A1 | 8/2005 | Heim et al. | 623/2.12 |
| 2005/0177228 A1 | 8/2005 | Solem et al. | 623/2.36 |
| 2005/0182483 A1 | 8/2005 | Osborne et al. | 623/1.24 |
| 2005/0184122 A1 | 8/2005 | Hlavka et al. | 227/175.1 |
| 2005/0187614 A1 | 8/2005 | Agnew | 623/1.24 |
| 2005/0187616 A1 | 8/2005 | Realyvasquez | 623/2.11 |
| 2005/0187617 A1 | 8/2005 | Navia | 623/2.13 |
| 2005/0192606 A1 | 9/2005 | Paul, Jr. et al. | 606/159 |
| 2005/0192665 A1 | 9/2005 | Spenser et al. | 623/2.11 |
| 2005/0197692 A1 | 9/2005 | Pai et al. | 623/2.1 |
| 2005/0197693 A1 | 9/2005 | Pai et al. | 623/2.1 |
| 2005/0197694 A1 | 9/2005 | Pai et al. | 623/2.1 |
| 2005/0203549 A1 | 9/2005 | Realyvasquez | 606/142 |
| 2005/0203605 A1 | 9/2005 | Dolan | 623/1.11 |
| 2005/0203614 A1 | 9/2005 | Forster et al. | 623/2.11 |
| 2005/0203615 A1 | 9/2005 | Forster et al. | 623/2.11 |
| 2005/0203616 A1 | 9/2005 | Cribier | 623/2.11 |
| 2005/0203617 A1 | 9/2005 | Forster et al. | 623/2.14 |

| Publication No. | Date | Inventor | Class |
|---|---|---|---|
| 2005/0203618 A1 | 9/2005 | Sharkawy et al. | 623/2.38 |
| 2005/0216039 A1 | 9/2005 | Lederman | 606/144 |
| 2005/0216077 A1 | 9/2005 | Mathis et al. | 623/2.11 |
| 2005/0216078 A1 | 9/2005 | Starksen et al. | 623/2.11 |
| 2005/0222675 A1 | 10/2005 | Sauter | 623/1.26 |
| 2005/0222678 A1 | 10/2005 | Lashinski et al. | 623/2.11 |
| 2005/0228422 A1 | 10/2005 | Machold et al. | 606/167 |
| 2005/0228479 A1 | 10/2005 | Pavcnik et al. | 623/1.11 |
| 2005/0228486 A1 | 10/2005 | Case et al. | 623/1.24 |
| 2005/0228494 A1 | 10/2005 | Marquez | 623/2.18 |
| 2005/0228495 A1 | 10/2005 | Macoviak | 623/2.18 |
| 2005/0228496 A1 | 10/2005 | Mensah et al. | 623/2.41 |
| 2005/0234541 A1 | 10/2005 | Hunt et al. | 623/1.24 |
| 2005/0234546 A1 | 10/2005 | Nugent et al. | 623/2.11 |
| 2005/0240200 A1 | 10/2005 | Bergheim | 606/108 |
| 2005/0240202 A1 | 10/2005 | Shennib et al. | 606/142 |
| 2005/0240255 A1 | 10/2005 | Schaeffer | 623/1.11 |
| 2005/0240259 A1 | 10/2005 | Sisken et al. | 623/1.36 |
| 2005/0240262 A1 | 10/2005 | White | 623/2.12 |
| 2005/0244460 A1 | 11/2005 | Alferiev et al. | 424/426 |
| 2005/0246013 A1 | 11/2005 | Gabbay | 623/2.1 |
| 2005/0251251 A1 | 11/2005 | Cribier | 623/2.11 |
| 2005/0256566 A1 | 11/2005 | Gabbay | 623/2.1 |
| 2005/0261704 A1 | 11/2005 | Mathis | 606/108 |
| 2005/0261759 A1 | 11/2005 | Lambrecht et al. | 623/1.26 |
| 2005/0267493 A1 | 12/2005 | Schreck et al. | 606/139 |
| 2005/0267560 A1 | 12/2005 | Bates | 623/1.1 |
| 2005/0267565 A1 | 12/2005 | Dave et al. | 623/1.15 |
| 2005/0267571 A1 | 12/2005 | Spence et al. | 623/2.11 |
| 2005/0267573 A9 | 12/2005 | Macoviak et al. | 623/2.36 |
| 2005/0267574 A1 | 12/2005 | Cohn et al. | 623/2.36 |
| 2005/0272969 A1 | 12/2005 | Alferness et al. | 600/37 |
| 2005/0273160 A1 | 12/2005 | Lashinski et al. | 623/1.25 |
| 2005/0278015 A1 | 12/2005 | Dave et al. | 623/1.38 |
| 2005/0283178 A1 | 12/2005 | Flagle et al. | 606/191 |
| 2005/0288779 A1 | 12/2005 | Shaoulian et al. | 623/2.37 |
| 2006/0000715 A1 | 1/2006 | Whitcher et al. | 205/80 |
| 2006/0004439 A1 | 1/2006 | Spenser et al. | 623/1.23 |
| 2006/0004442 A1 | 1/2006 | Spenser et al. | 623/2.11 |
| 2006/0009841 A1 | 1/2006 | McGuckin, Jr. et al. | 623/2.38 |
| 2006/0009842 A1 | 1/2006 | Huynh et al. | 623/2.41 |
| 2006/0013805 A1 | 1/2006 | Hebbel et al. | 424/93.21 |
| 2006/0013855 A1 | 1/2006 | Carpenter et al. | 424/423 |
| 2006/0015136 A1 | 1/2006 | Besselink | 606/200 |
| 2006/0015178 A1 | 1/2006 | Moaddeb et al. | 623/2.36 |
| 2006/0015179 A1 | 1/2006 | Bulman-Fleming et al. | 623/2.36 |
| 2006/0020275 A1 | 1/2006 | Goldfarb et al. | 606/151 |
| 2006/0020327 A1 | 1/2006 | Lashinski et al. | 623/1.25 |
| 2006/0020332 A1 | 1/2006 | Lashinski et al. | 623/2.11 |
| 2006/0020334 A1 | 1/2006 | Lashinski et al. | 623/2.11 |
| 2006/0020335 A1 | 1/2006 | Kowalsky et al. | 623/2.36 |
| 2006/0020336 A1 | 1/2006 | Liddicoat | 623/2.37 |
| 2006/0025750 A1 | 2/2006 | Starksen et al. | 604/510 |
| 2006/0025784 A1 | 2/2006 | Starksen et al. | 606/151 |
| 2006/0025787 A1 | 2/2006 | Morales et al. | 606/151 |
| 2006/0025854 A1 | 2/2006 | Lashinski et al. | 623/1.25 |
| 2006/0025855 A1 | 2/2006 | Lashinski et al. | 623/2.1 |
| 2006/0025856 A1 | 2/2006 | Ryan et al. | 623/2.11 |
| 2006/0025857 A1 | 2/2006 | Bergheim et al. | 623/2.18 |
| 2006/0030747 A1 | 2/2006 | Kantrowitz et al. | 600/16 |
| 2006/0030866 A1 | 2/2006 | Schreck | 606/139 |
| 2006/0030882 A1 | 2/2006 | Adams et al. | 606/219 |
| 2006/0030885 A1 | 2/2006 | Hyde | 606/232 |
| 2006/0036317 A1 | 2/2006 | Vidlund et al. | 623/2.36 |
| 2006/0041305 A1 | 2/2006 | Lauterjung | 623/1.36 |
| 2006/0041306 A1 | 2/2006 | Vidlund et al. | 623/2.11 |
| 2006/0047297 A1 | 3/2006 | Case | 606/194 |
| 2006/0047338 A1 | 3/2006 | Jenson | 623/2.11 |
| 2006/0047343 A1 | 3/2006 | Oviatt et al. | 623/915 |
| 2006/0052804 A1 | 3/2006 | Mialhe | 606/157 |
| 2006/0052867 A1 | 3/2006 | Revuelta et al. | 623/2.18 |
| 2006/0058817 A1 | 3/2006 | Starksen et al. | 606/142 |
| 2006/0058865 A1 | 3/2006 | Case et al. | 623/1.11 |
| 2006/0058871 A1 | 3/2006 | Zakay et al. | 623/2.18 |
| 2006/0058889 A1 | 3/2006 | Case et al. | 623/23.68 |
| 2006/0064115 A1 | 3/2006 | Allen et al. | 606/139 |
| 2006/0064116 A1 | 3/2006 | Allen et al. | 606/139 |
| 2006/0064118 A1 | 3/2006 | Kimblad | 606/151 |
| 2006/0064174 A1 | 3/2006 | Zadno | 623/23.68 |
| 2006/0069400 A1 | 3/2006 | Burnett et al. | 606/153 |
| 2006/0069430 A9 | 3/2006 | Rahdert et al. | 623/2.36 |
| 2006/0074483 A1 | 4/2006 | Schrayer | 623/2.1 |
| 2006/0074484 A1 | 4/2006 | Huber | 623/2.11 |
| 2006/0074485 A1 | 4/2006 | Realyvasquez | 623/2.11 |
| 2006/0085060 A1 | 4/2006 | Campbell | 623/1.26 |
| 2006/0089708 A1 | 4/2006 | Osse et al. | 623/1.24 |
| 2006/0095115 A1 | 5/2006 | Bladillah et al. | 623/1.16 |
| 2006/0095125 A1 | 5/2006 | Chinn et al. | 623/2.4 |
| 2006/0099326 A1 | 5/2006 | Keogh et al. | 427/2.36 |
| 2006/0100697 A1 | 5/2006 | Casanova | 623/2.11 |
| 2006/0100699 A1 | 5/2006 | Vidlund et al. | 623/2.36 |
| 2006/0106278 A1 | 5/2006 | Machold et al. | 600/37 |
| 2006/0106279 A1 | 5/2006 | Machold et al. | 600/37 |
| 2006/0106456 A9 | 5/2006 | Machold et al. | 623/2.36 |
| 2006/0111660 A1 | 5/2006 | Wolf et al. | 604/9 |
| 2006/0111773 A1 | 5/2006 | Rittgers et al. | 623/1.24 |
| 2006/0111774 A1 | 5/2006 | Samkov et al. | 623/2.25 |
| 2006/0116572 A1 | 6/2006 | Case | 600/424 |
| 2006/0116756 A1 | 6/2006 | Solem et al. | 623/2.11 |
| 2006/0122686 A1 | 6/2006 | Gilad et al. | 623/1.13 |
| 2006/0122692 A1 | 6/2006 | Gilad et al. | 623/1.24 |
| 2006/0122693 A1 | 6/2006 | Biadillah et al. | 623/1.24 |
| 2006/0127443 A1 | 6/2006 | Helmus | 424/423 |
| 2006/0129235 A1 | 6/2006 | Seguin et al. | 623/2.11 |
| 2006/0129236 A1 | 6/2006 | McCarthy | 623/2.36 |
| 2006/0135476 A1 | 6/2006 | Kutryk et al. | 514/59 |
| 2006/0135964 A1 | 6/2006 | Vesely | 606/108 |
| 2006/0135967 A1 | 6/2006 | Realyvasquez | 606/142 |
| 2006/0136044 A1 | 6/2006 | Osborne | 623/1.24 |
| 2006/0136045 A1 | 6/2006 | Flagle et al. | 623/1.24 |
| 2006/0136052 A1 | 6/2006 | Vesely | 623/2.18 |
| 2006/0136054 A1 | 6/2006 | Berg et al. | 623/2.38 |
| 2006/0142846 A1 | 6/2006 | Pavcnik et al. | 623/1.24 |
| 2006/0142847 A1 | 6/2006 | Shaknovich | 623/1.24 |
| 2006/0142848 A1 | 6/2006 | Gabbay | 623/1.26 |
| 2006/0142854 A1 | 6/2006 | Alferness et al. | 623/2.11 |
| 2006/0149358 A1 | 7/2006 | Zilla et al. | 623/1.22 |
| 2006/0149360 A1 | 7/2006 | Schwammenthal et al. | 623/1.24 |
| 2006/0149367 A1 | 7/2006 | Sieracki | 623/2.21 |
| 2006/0149368 A1 | 7/2006 | Spence | 623/2.37 |
| 2006/0161133 A1 | 7/2006 | Laird et al. | 604/509 |
| 2006/0161248 A1 | 7/2006 | Case et al. | 623/2.1 |
| 2006/0161250 A1 | 7/2006 | Shaw | 623/2.17 |
| 2006/0167468 A1 | 7/2006 | Gabbay | 606/108 |
| 2006/0167541 A1 | 7/2006 | Lattouf | 623/2.11 |
| 2006/0167542 A1 | 7/2006 | Quintessenza | 623/2.12 |
| 2006/0167543 A1 | 7/2006 | Bailey et al. | 623/2.18 |

FOREIGN PATENT DOCUMENTS

| | | |
|---|---|---|
| FR | 2 728 457 | 6/1996 |
| WO | WO 88/00459 | 1/1988 |
| WO | WO 90/15582 | 12/1990 |
| WO | WO 95/01669 | 1/1995 |
| WO | WO 96/19159 | 6/1996 |
| WO | WO 98/03656 | 1/1998 |
| WO | WO 98/46115 | 10/1998 |
| WO | WO 99/04724 | 2/1999 |
| WO | WO 00/67679 | 11/2000 |
| WO | WO 01/15650 | 3/2001 |
| WO | WO 01/17462 | 3/2001 |
| WO | WO 03/047468 | 6/2003 |
| WO | WO 03/084443 | 10/2003 |
| WO | WO 2004/019825 | 3/2004 |
| WO | WO 2004/021893 | 3/2004 |
| WO | WO 2004/023980 | 3/2004 |
| WO | WO 2004/030568 | 4/2004 |
| WO | WO 2004/030569 | 4/2004 |
| WO | WO 2004/030570 | 4/2004 |
| WO | WO 2004/032724 | 4/2004 |
| WO | WO 2004/032796 | 4/2004 |
| WO | WO 2004/037128 | 5/2004 |
| WO | WO 2004/037317 | 5/2004 |
| WO | WO 2004/039432 | 5/2004 |
| WO | WO 2004/043265 | 5/2004 |
| WO | WO 2004/043273 | 5/2004 |
| WO | WO 2004/043293 | 5/2004 |
| WO | WO 2004/045370 | 6/2004 |

| | | | | | | |
|---|---|---|---|---|---|---|
| WO | WO 2004/045378 | 6/2004 | | WO | WO 2005/046529 | 5/2005 |
| WO | WO 2004/045463 | 6/2004 | | WO | WO 2005/046530 | 5/2005 |
| WO | WO 2004/047677 | 6/2004 | | WO | WO 2005/046531 | 5/2005 |
| WO | WO 2004/060217 | 7/2004 | | WO | WO 2005/048883 | 6/2005 |
| WO | WO 2004/060470 | 7/2004 | | WO | WO 2005/049103 | 6/2005 |
| WO | WO 2004/062725 | 7/2004 | | WO | WO 2005/051226 | 6/2005 |
| WO | WO 2004/066803 | 8/2004 | | WO | WO 2005/055811 | 6/2005 |
| WO | WO 2004/066826 | 8/2004 | | WO | WO 2005/055883 | 6/2005 |
| WO | WO 2004/069287 | 8/2004 | | WO | WO 2005/058206 | 6/2005 |
| WO | WO 2004/075789 | 9/2004 | | WO | WO 2005/065585 | 7/2005 |
| WO | WO 2004/080352 | 9/2004 | | WO | WO 2005/065593 | 7/2005 |
| WO | WO 2004/082523 | 9/2004 | | WO | WO 2005/065594 | 7/2005 |
| WO | WO 2004/082527 | 9/2004 | | WO | WO 2005/070342 | 8/2005 |
| WO | WO 2004/082528 | 9/2004 | | WO | WO 2005/070343 | 8/2005 |
| WO | WO 2004/082536 | 9/2004 | | WO | WO 2005/072654 | 8/2005 |
| WO | WO 2004/082537 | 9/2004 | | WO | WO 2005/072655 | 8/2005 |
| WO | WO 2004/082538 | 9/2004 | | WO | WO 2005/079706 | 9/2005 |
| WO | WO 2004/082757 | 9/2004 | | WO | WO 2005/082288 | 9/2005 |
| WO | WO 2004/084770 | 10/2004 | | WO | WO 2005/082289 | 9/2005 |
| WO | WO 2004/084786 | 10/2004 | | WO | WO 2005/084595 | 9/2005 |
| WO | WO 2004/089246 | 10/2004 | | WO | WO 2005/087139 | 9/2005 |
| WO | WO 2004/089250 | 10/2004 | | WO | WO 2005/087140 | 9/2005 |
| WO | WO 2004/089253 | 10/2004 | | WO | WO 2006/000763 | 1/2006 |
| WO | WO 2004/091449 | 10/2004 | | WO | WO 2006/000776 | 1/2006 |
| WO | WO 2004/091454 | 10/2004 | | WO | WO 2006/002492 | 1/2006 |
| WO | WO 2004/093638 | 11/2004 | | WO | WO 2006/004679 | 1/2006 |
| WO | WO 2004/093726 | 11/2004 | | WO | WO 2006/005015 | 1/2006 |
| WO | WO 2004/093728 | 11/2004 | | WO | WO 2006/009690 | 1/2006 |
| WO | WO 2004/093730 | 11/2004 | | WO | WO 2006/011127 | 2/2006 |
| WO | WO 2004/093745 | 11/2004 | | WO | WO 2006/012011 | 2/2006 |
| WO | WO 2004/093935 | 11/2004 | | WO | WO 2006/012013 | 2/2006 |
| WO | WO 2004/096100 | 11/2004 | | WO | WO 2006/012038 | 2/2006 |
| WO | WO 2004/103222 | 12/2004 | | WO | WO 2006/012068 | 2/2006 |
| WO | WO 2004/103223 | 12/2004 | | WO | WO 2006/012322 | 2/2006 |
| WO | WO 2004/105584 | 12/2004 | | WO | WO 2006/019498 | 2/2006 |
| WO | WO 2004/105651 | 12/2004 | | WO | WO 2006/026371 | 3/2006 |
| WO | WO 2004/112582 | 12/2004 | | WO | WO 2006/026377 | 3/2006 |
| WO | WO 2004/112585 | 12/2004 | | WO | WO 2006/026912 | 3/2006 |
| WO | WO 2004/112643 | 12/2004 | | WO | WO 2006/027499 | 3/2006 |
| WO | WO 2004/112652 | 12/2004 | | WO | WO 2006/028821 | 3/2006 |
| WO | WO 2004/112657 | 12/2004 | | WO | WO 2006/029062 | 3/2006 |
| WO | WO 2004/112658 | 12/2004 | | WO | WO 2006/031436 | 3/2006 |
| WO | WO 2005/000152 | 1/2005 | | WO | WO 2006/031469 | 3/2006 |
| WO | WO 2005/002424 | 1/2005 | | WO | WO 2006/032051 | 3/2006 |
| WO | WO 2005/002466 | 1/2005 | | WO | WO 2006/034245 | 3/2006 |
| WO | WO 2005/004753 | 1/2005 | | WO | WO 2006/035415 | 4/2006 |
| WO | WO 2005/007017 | 1/2005 | | WO | WO 2006/041505 | 4/2006 |
| WO | WO 2005/007018 | 1/2005 | | WO | WO 2006/044679 | 4/2006 |
| WO | WO 2005/007036 | 1/2005 | | WO | WO 2006/048664 | 5/2006 |
| WO | WO 2005/007037 | 1/2005 | | WO | WO 2006/050459 | 5/2006 |
| WO | WO 2005/009285 | 2/2005 | | WO | WO 2006/050460 | 5/2006 |
| WO | WO 2005/009286 | 2/2005 | | WO | WO 2006/054107 | 5/2006 |
| WO | WO 2005/009505 | 2/2005 | | WO | WO 2006/054930 | 5/2006 |
| WO | WO 2005/009506 | 2/2005 | | WO | WO 2006/055982 | 5/2006 |
| WO | WO 2005/011473 | 2/2005 | | WO | WO 2006/060546 | 6/2006 |
| WO | WO 2005/011534 | 2/2005 | | WO | WO 2006/063108 | 6/2006 |
| WO | WO 2005/011535 | 2/2005 | | WO | WO 2006/063181 | 6/2006 |
| WO | WO 2005/013860 | 2/2005 | | WO | WO 2006/063199 | 6/2006 |
| WO | WO 2005/018507 | 3/2005 | | WO | WO 2006/064490 | 6/2006 |
| WO | WO 2005/021063 | 3/2005 | | WO | WO 2006/065212 | 6/2006 |
| WO | WO 2005/023155 | 3/2005 | | WO | WO 2006/065930 | 6/2006 |
| WO | WO 2005/025644 | 3/2005 | | WO | WO 2006/066148 | 6/2006 |
| WO | WO 2005/027790 | 3/2005 | | WO | WO 2006/066150 | 6/2006 |
| WO | WO 2005/027797 | 3/2005 | | WO | WO 2006/069094 | 6/2006 |
| WO | WO 2005/034812 | 4/2005 | | WO | WO 2006/070372 | 7/2006 |
| WO | WO 2005/039428 | 5/2005 | | WO | WO 2006/073628 | 7/2006 |
| WO | WO 2005/039452 | 5/2005 | | WO | WO 2006/076890 | 7/2006 |
| WO | WO 2005/045488 | 5/2005 | | | | |
| WO | WO 2005/046528 | 5/2005 | | * cited by examiner | | |

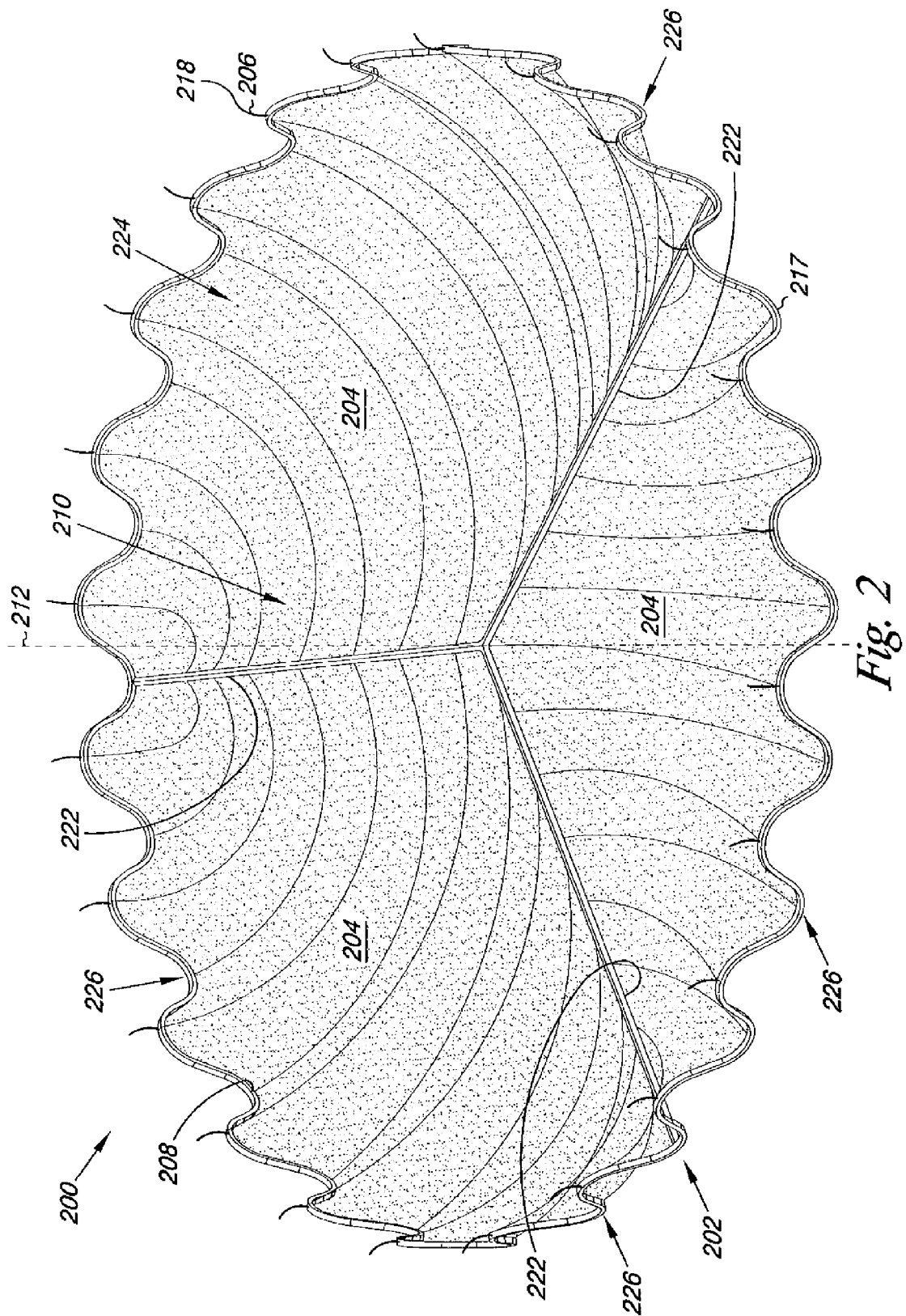

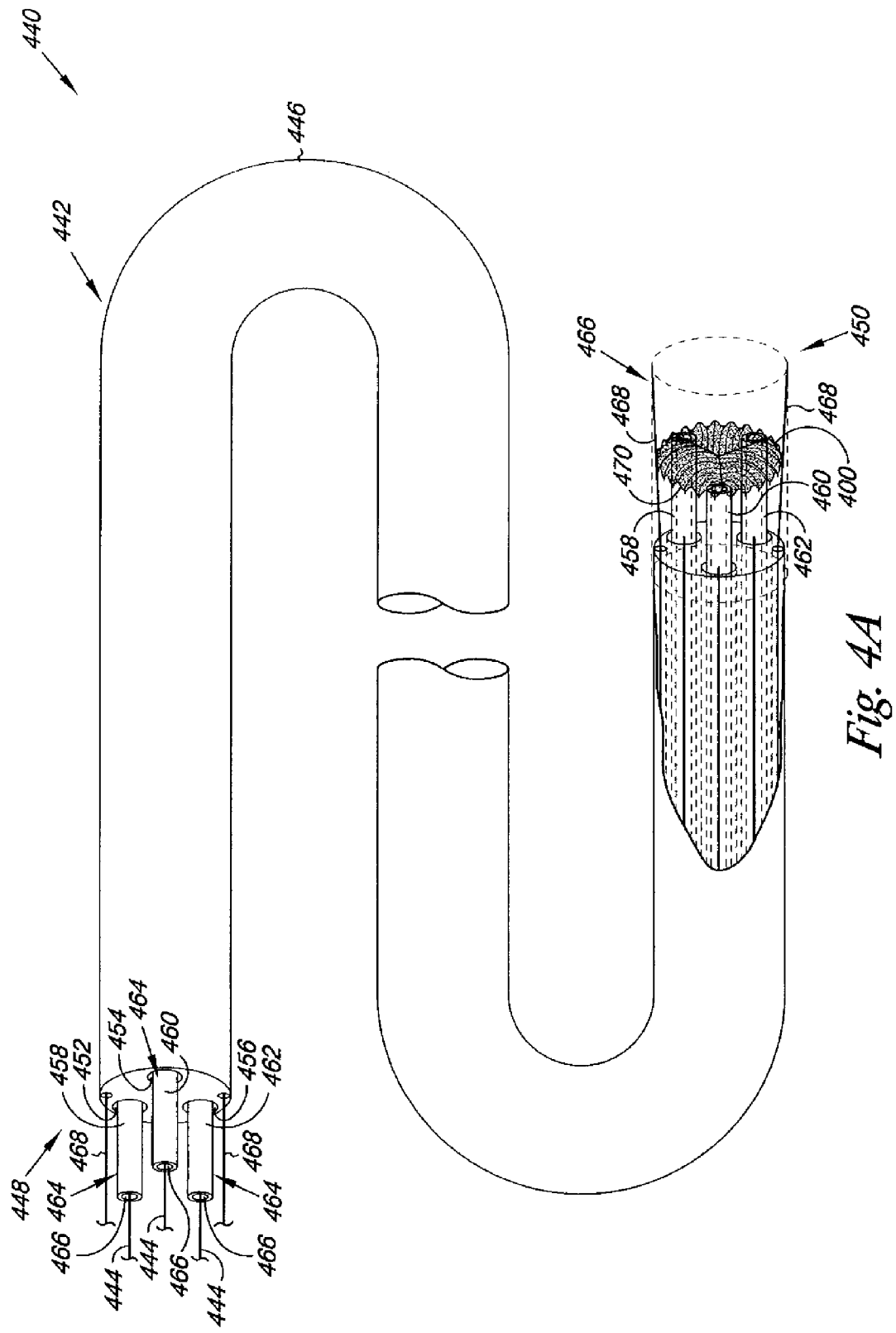

VALVE APPARATUS, SYSTEM AND METHOD

CROSS-REFERENCE TO RELATED APPLICATION

This application is a continuation of U.S. application Ser. No. 11/107,162 filed Apr. 15, 2005, the entire content of which is incorporated herein by reference.

FIELD OF THE INVENTION

The present invention relates generally to apparatus, systems, and methods for use in a lumen; and more particularly to a valve apparatus, systems, and methods for use in the vasculature system.

BACKGROUND OF THE INVENTION

Diseases of the heart valves are grouped according to which valve(s) are involved and the way blood flow is disrupted. The most common valve problems occur in the mitral and aortic valves. Diseases of the tricuspid and pulmonary valves are fairly rare.

The aortic valve regulates the blood flow from the heart's left ventricle into the aorta. The aorta is the main vessel that supplies oxygenated blood to the rest of the body. Diseases of the aorta can have a significant impact on an individual. Examples of such diseases include aortic regurgitation and aortic stenosis.

Aortic regurgitation is also called aortic insufficiency or aortic incompetence. It is a condition in which blood flows backward from a widened or weakened aortic valve into the left ventricle of the heart. In its most serious form, aortic regurgitation is caused by an infection that leaves holes in the valve leaflets. Symptoms of aortic regurgitation may not appear for years. When symptoms do appear, it is because the left ventricle must work harder as compared to an uncompromised ventricle to make up for the backflow of blood. The ventricle eventually gets larger and fluid backs up.

Aortic stenosis is a narrowing or blockage of the aortic valve. Aortic stenosis occurs when the valve leaflets of the aorta become coated with deposits. The deposits change the shape of the leaflets and reduce blood flow through the valve. The left ventricle has to work harder as compared to an uncompromised ventricle to make up for the reduced blood flow. Over time, the extra work can weaken the heart muscle.

BRIEF DESCRIPTION OF THE DRAWINGS

FIG. 2 illustrates an embodiment of a valve.
FIGS. 4A-4C illustrate an embodiment of a system that includes a valve.

DETAILED DESCRIPTION

Figure 1A:
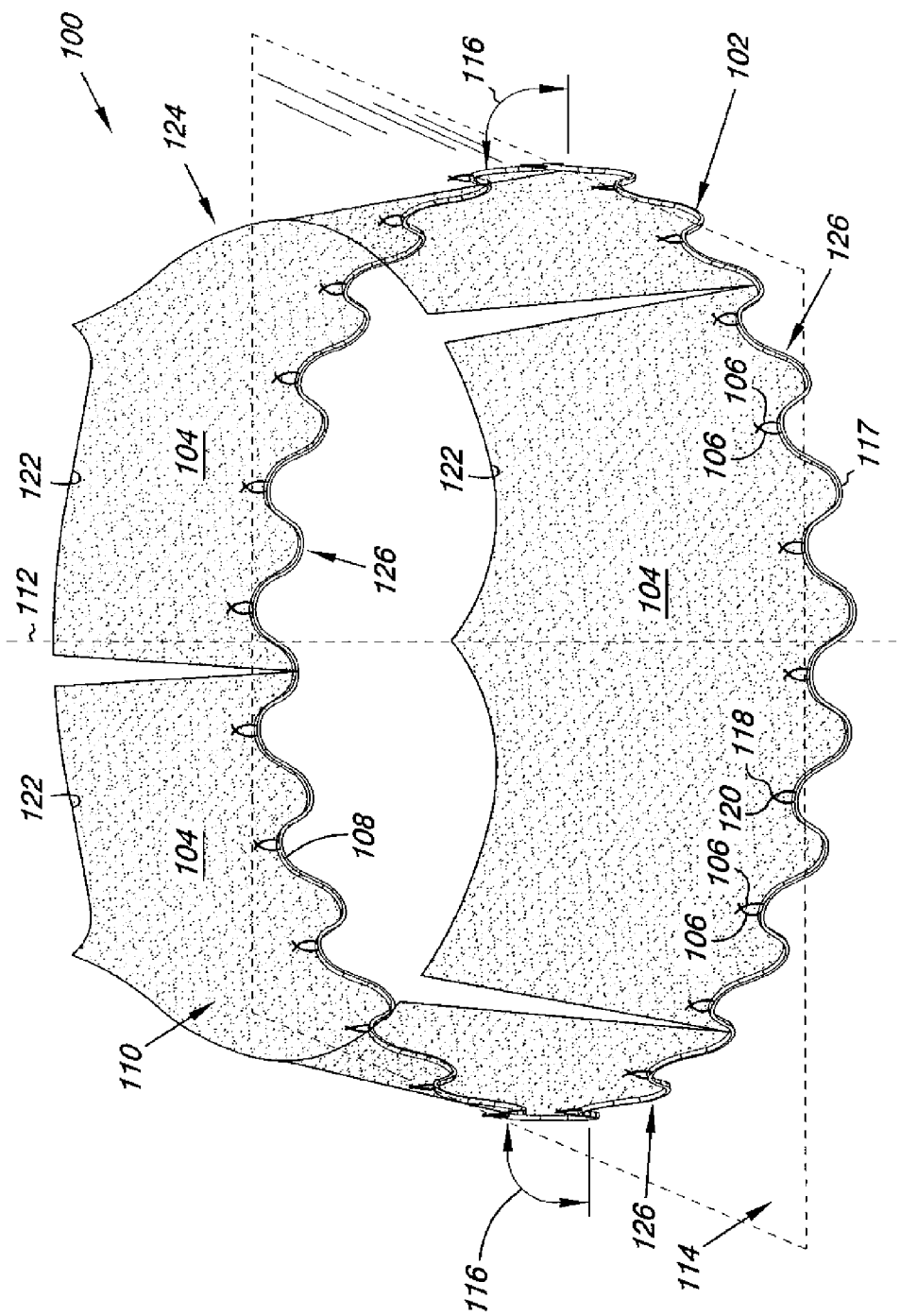
FIGS. 1A and 1B illustrate an embodiment of a valve.

Embodiments of the present invention are directed to an apparatus, system, and method for percutaneous cardiac valve replacement and/or augmentation. For example, the apparatus can include a cardiac valve that can be used to replace an incompetent valve (e.g., an aortic valve, a mitral valve, a tricuspid valve or a pulmonary valve) in a body lumen. Embodiments of the cardiac valve can include a first anchor frame and two or more leaflets that can be implanted through minimally-invasive techniques into a body lumen, such as an artery or a vein. In one example, embodiments of the present invention may help to augment or replace the function of a cardiac valve of individuals having heart valve disease.

The Figures herein follow a numbering convention in which the first digit or digits correspond to the drawing Figure number and the remaining digits identify an element or component in the drawing. Similar elements or components between different Figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve. In addition, as will be appreciated the proportion and the relative scale of the elements provided in the figures are intended to illustrate the embodiments of the present invention, and should not be taken in a limiting sense.

Various embodiments of the invention are illustrated in the figures. Generally, the cardiac valve can be implanted within the fluid passageway of a body lumen, such as for replacement or augmentation of a cardiac valve structure within the body lumen (e.g., an aortic valve at the aortic root), to regulate the flow of a bodily fluid through the body lumen in a single direction. The embodiments of the cardiac valve of the present invention attempt to maximize the effective area of the opening through the cardiac valve. In addition to maximizing the effective area of the opening, the valve leaflets used with the cardiac valve are believed to provide an improvement in the hemodynamics performance of the cardiac valve. For example, it is believed that the embodiments of the present invention help to increase the area of the outflow through the valve, and thus provide for a lower pressure gradient across the valve. As such, embodiments of the present invention are believed to provide not only a large effective flow area relative the total area covered by the valve, but also improved hemodynamic performance of the cardiac valve.

Figure 1B:
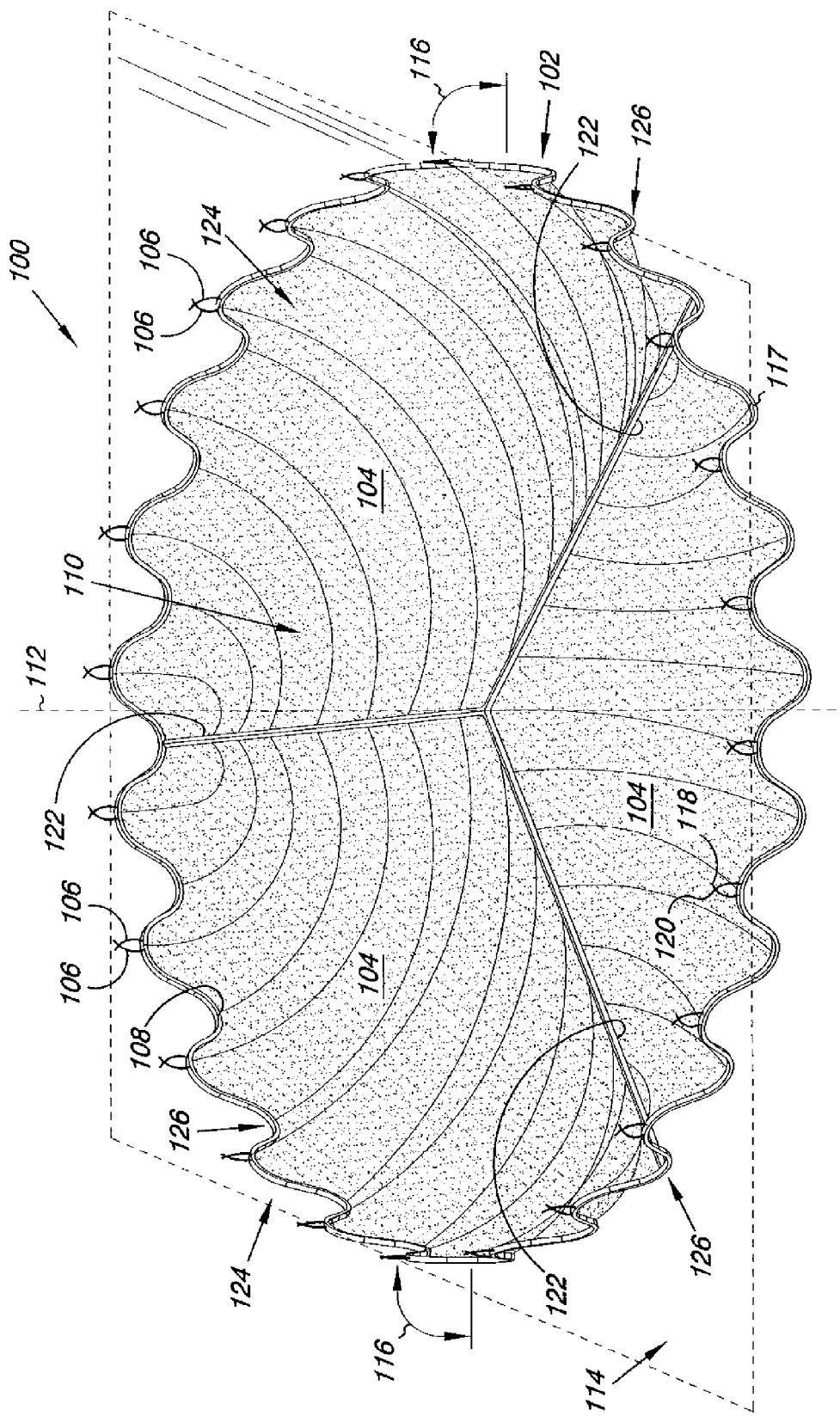

FIGS. 1A and 1B illustrate one embodiment of a cardiac valve 100. FIGS. 1A and 1B provide a perspective illustration of valve 100 in an open configuration (FIG. 1A) and a closed configuration (FIG. 1B). Cardiac valve 100 includes a first anchor frame 102, two or more leaflets 104, and two or more anchor members 106. The first anchor frame 102 includes a surface 108 defining an opening 110 through the first anchor frame 102. The leaflets 104 are coupled to the first anchor frame 102, as will be discussed herein, where the leaflets 104 can repeatedly move between an open state (FIG. 1A) and a closed state (FIG. 1B) for unidirectional flow of a liquid through the opening 110 of the cardiac valve 100.

As illustrated, the anchor members 106 extend vertically over the surface 108 defining the opening 110 through the first anchor frame 102 when the cardiac valve 100 is in its fully deployed configuration. For example, in one embodiment the anchoring members 106 extend parallel with a common axis 112 that is perpendicular to a common plane 114 extending through the first anchor frame 102. In an additional embodiment, the anchoring members 106 can extend at an acute angle 116 relative the common plane 114 extending through the first anchor frame 102.

The first anchor frame 102 can, in addition, have a variety of flexible configurations and be formed from a variety of materials. For example, the first anchor frame 102 can have an overall ring like configuration taken along the common plane 114, where the ring is radially compressible due the zigzag and/or serpentine configuration of the frame 102. As will be appreciated, the ring like configuration can include, but is not limited to, circular, elliptical, and variations on those shapes that may be useful in allowing the shape of the first anchor frame 102 to more closely conform to the physiological shape (e.g., the fibrous ring surrounding the orifice of the cardiac valve that is being augmented or replaced) and/or environment into which the cardiac valve 100 is being implanted. In addition, as will be appreciated the flexible configuration is not limited to the zigzag and/or serpentine configuration, but is only used as one illustration of such a flexible configuration. As such, the present invention should not be limited to the illustration of the first anchor frame 102. In addition, the first anchor frame 102 need not necessarily have a planar configuration, but can also include non-planar configurations as necessary to best conform to the native physiological shape and/or environment into which the cardiac valve 100 is being implanted.

The first anchor frame 102 can also be configured to display a minimal surface area relative the surface area common plane 114. In one embodiment, this minimal surface area can be tailored to match to the surface area of the fibrous ring surrounding the orifice of the cardiac valve that is being augmented or replaced with the cardiac valve 100. In this way, the amount of surface area for the opening 110 of the cardiac valve 100 can more closely match the surface area of the opening for the native cardiac valve that is being replaced or augmented. In other words, the first anchor frame 102 can have a predetermined circumference that allows for sufficient contact with the fibrous ring surrounding the orifice of the cardiac valve while maximizing the surface area of the opening of the cardiac valve 100.

In one embodiment, the first anchor frame 102 can be formed of one or more frame members 117. The frame members 117 can also have dimensions that assist in providing the first anchor frame 102 with the minimal surface area relative the surface area common plane 114. The exact dimensions for the frame members 117 will depend upon their cross-sectional shape and also their configuration. In one embodiment, the surface area of the opening 110 can be from 3.0 cm$^2$ to 4.0 cm$^2$. As will be appreciated, the exact surface area of the opening 110 will be determined based on the specific patient.

In addition, the cardiac valve 100 can have a diameter from 15 mm to 36 mm, which exact size will be dependent upon the size and type of valve being replaced. The frame members 117 can have a diameter from 0.07 mm to 0.51 mm depending on the valve support material and the target anatomy. The valve 100 can also include a height from 1 cm to 6 cm depending on the valve being replaced and patient size.

The frame members 117 can have one or more of a variety of cross-sectional shapes and dimensions. For example, the frame members 117 can have a tubular and/or a solid cross-sectional configuration. In addition, the frame members 117 can have cross-sectional shapes that include, but are not limited to, circular, elliptical or oval, I-shaped, T-shaped, triangular, rectangular, and/or polygonal (i.e., multi-sided shapes). The members can also have a single cross-sectional shape (e.g., all members of frame 102 can have a circular cross-sectional shape). In an additional embodiment, the members of the first anchor frame 102 can include two or more cross-sectional shapes. In addition, the type of delivery technique that will be used with the cardiac valve 100, as discussed herein, can also have an influence on the shape and configuration of the first anchor frame 102 used with the cardiac valve 100.

The frame members 117 of the first anchor frame 102 can be formed from a wide variety of materials. Generally, the first anchor frame 102 has a unitary structure that can have a configuration that allows the frame 102 to be radially expandable through the use of a balloon catheter, as will be discussed herein. In an alternative embodiment, the first anchor frame 102 can also be self-expanding. Examples of self-expanding frames include those formed from temperature-sensitive memory alloy which changes shape at a designated temperature or temperature range. Alternatively, the self-expanding frames can include those having a spring-bias.

The first anchor frame 102 can be formed from any number of materials. For example, the first anchor frame 102 can be formed from a biocompatible metal, metal alloy, polymeric material, or combination thereof. As discussed herein, the first anchor frame 102 can be self-expanding or balloon expandable. In addition, the first anchor frame can be configured so as to have the ability to move radially between the collapsed state and the expanded state. To accomplish this, the material used to form the first anchor frame should exhibit a low elastic modulus and a high yield stress for large elastic strains that can recover from elastic deformations. Examples of suitable materials include, but are not limited to, medical grade stainless steel (e.g., 316L), titanium, tantalum, platinum alloys, niobium alloys, cobalt alloys, alginate, or combinations thereof. Additional anchor frame embodiments may be formed from a shape-memory material, such as shape memory plastics, polymers, and thermoplastic materials which are inert in the body. Shaped memory alloys having superelastic properties generally made from ratios of nickel and titanium, commonly known as Nitinol, are also possible materials. Other materials are also possible.

The frame members 117 of the first anchor frame 102 can also be shaped, joined and/or formed in a variety of ways. For example, a single contiguous member can be bent around a tubular mandrel to form the first anchor frame 102. The free ends of the single contiguous member can then be welded, fused, crimped, or otherwise joined together to form the first anchor frame 102. Alternatively, the first anchor frame 102 can be derived (e.g., laser cut, water cut) from a single tubular segment. The first anchor frame 102 can be annealed to relieve internal stress and subsequently polished by methods as is typically known for the material which forms the first anchor frame 102.

In addition, the anchor members 106 can also be joined and/or formed from the frame members 117 of the first anchor frame 102. For example, anchor members 106 can be separately formed from and then attached to the first anchor frame 102. The anchor members 106 can be welded, fused, crimped, or otherwise joined to the first anchor frame 102 as described herein. In an additional embodiment, the anchor members 106 can be formed from at least a portion of the frame members 117. For example, segments of the frame members 117 could be cut and then bent so as to form the anchor members 106 extending vertically over the surface 108 defining the opening 110 through the first anchor frame 102, as discussed herein.

As illustrated in FIGS. 1A and 1B, the anchor members 106 can each include a first end 118 and a second end 120. The first and second ends 118 and 120 each have a size and configuration that are adapted to both penetrate tissue (e.g., the fibrous tissue that surrounds cardiac valves) and to anchor the cardiac valve 100 to the tissue.

A variety of structures and configurations of the anchor members 106 are available for anchoring the cardiac valve 100 to the tissue. For example, one or both of the first end 118 and the second end 120 can include a barb for penetrating and anchoring the cardiac valve 100 to the tissue. In an additional embodiment, the anchor members 106 can have material characteristics that allow the cardiac valve 100 to be secured to the cardiac tissue. For example, the anchor members 106 can be constructed and shaped in such a way that the first and second ends 118 and 120 of the anchor members 106 have a driving force to move from a first predetermined shape to a second predetermined shape to anchor the cardiac valve 100 to tissues. In one embodiment, this movement can be on account of the first and second ends 118 and 120 of the anchor members 106 being restrained or held in the first predetermined position under tension. When no longer restrained, the first and second ends 118 and 120 of the anchor members 106 move back towards the second predetermined position. An embodiment of the second predetermined position is illustrated in FIGS. 1A and 1B. In one embodiment, the first and second ends 118 and 120 are held in tension due to the presence of a deployment member that can be removed from between the first and second ends 118 and 120, as will be discussed more fully herein.

The anchor members 106 can also have a variety of shapes that allow for the first and second ends 118 and 120 to be held under tension, as will be discussed more fully herein. For example, the anchor members 106 can be held under tension so as to have an overall U-shaped configuration, an overall square configuration (e.g., an un-bend staple configuration), and/or V-shaped configuration. After removing the restraint, one or both of the first and second ends 118 and 120 moves relative to each other to anchor the cardiac valve 100 to the cardiac tissue. For example, one or both of the first and second ends 118 and 120 can move towards each other thereby trapping and/or compressing tissue in their travel path. Alternatively, the first and second ends 118 and 120 can move so as to pierce through a portion of the cardiac tissue so as to embed barbs on the first and second ends 118 and 120 more fully into the cardiac tissue. In an additional example, the first and second ends 118 and 120 can move to provide a hooked end portion (i.e., a J-shaped end) of the anchor member 106. Other shapes and configurations are also possible.

The anchor members 106 can be formed from a wide variety of materials, such as those described herein for the first anchor frame 102 (e.g., stainless steel, nitinol). In addition, the anchor members 106 held under tension extend over the surface 108 of the first anchor frame 102, as discussed herein, by a predetermined distance. In one embodiment, the predetermined distance is sufficient to allow the first and second ends 118 and 120 of the anchor members 106 to engage the cardiac tissue (e.g., the fibrous ring surrounding the cardiac valve) sufficiently well so that when the deployment member, discussed herein, is removed the motion of the first and second ends 118 and 120 draws the anchor members 106 further into the cardiac tissue. As such, the length of the anchor members 106 used for the cardiac valve 100 will be dependent upon the implant location of the valve 100.

While the anchor members 106 are shown positioned completely around the first anchor frame 102, other placement configurations for the anchor members 106 are possible. For example, the anchor members 106 may be equally spaced around the first anchor frame 102. Alternatively, the anchor members 106 may be unequally spaced around the first anchor frame 102, where portions of the first anchor frame 102 may have relatively few or no anchor members 106 as compared to similar sized areas on the first anchor frame 102. In other words, there may be regions of the first anchor frame 102 where there are gaps in the placement of the anchor members 106. In one embodiment, this can be done to accommodate the physiological environment into which the cardiac valve 100 is to be implanted. For example, the region of the cardiac valve may not present enough fibrous tissue, or it may be too small of an area, to effectively implant the anchor members 106.

The cardiac valve 100 can further include one or more radiopaque markers (e.g., tabs, sleeves, welds). For example, one or more portions of the first anchor frame 102 can be formed from a radiopaque material. Radiopaque markers can be attached to and/or coated onto one or more locations along the first anchor frame 102. Examples of radiopaque material include, but are not limited to, gold, tantalum, and platinum. The position of the one or more radiopaque markers can be selected so as to provide information on the position, location and orientation of the valve 100 during its implantation.

The cardiac valve 100 further includes leaflets 104 having surfaces defining a reversibly sealable opening 122 for unidirectional flow of a liquid through the valve 100. For example, the leaflets 104 can be coupled to the first anchor member 102 so as to span and control fluid flow through the opening 110 of the cardiac valve 100. In one embodiment, the leaflets 104 can be derived from a xenograft cardiac valve. As will be appreciated, sources for xenograft cardiac valves include, but are not limited to, mammalian sources such as porcine, equine, and sheep.

In one embodiment, the leaflets 104 are provided by a valve root 124 derived from the xenographic donor. The valve root 124 includes the leaflets 104 of the valve along with a segment of the native valve with which to couple to the first anchor frame 102. For example, the valve root 124 can include an aortic root that includes both the leaflets and the segment of the aortic root sufficiently large enough to allow the aortic root to be coupled to the first anchor frame 102. Other valve roots besides the aortic root can be used with the embodiments of the present invention (e.g., a mitral valve root having two leaflets).

The valve root 124 can be mounted to the first anchor frame 102 in a variety of ways. For example, the first anchor frame 102 can include a sewing cushion 126 to which the valve root 124 can be attached. In one embodiment, the sewing cushion 126 can be coupled to the surface 108 of the first anchor frame 102 adjacent the anchor members 106. In an alternative embodiment, the sewing cushion 126 can be coupled to the surface 108 of the first anchor frame 102 where the sewing cushion 126 extends around the anchor members 106 so as not to interfere with their function. In an additional embodiment, the sewing cushion 126 can have a porous structure to allow for the in growth of tissue into the fabric.

The valve root 124 can then be coupled to the first anchor frame 102 in a number of ways that allow the leaflets 104 to be functionally positioned within the opening 110 of the cardiac valve 100. In one embodiment, the valve root 124 can be stitched to the sewing cushion 126 so that the valve root 124 is positioned completely within a perimeter defined by the anchoring members 106. Alternatively, the valve root 124 could be modified so as to be positioned at least partially on the sewing cushion while also being at least partially positioned around the anchoring members 106.

In addition to stitching, there are other techniques may be employed to secure the leaflets 104/valve root 124 to the first anchor frame 102 including the sewing cushion 126. These techniques can include, but are not limited to, the use of fasteners (such as biocompatible staples, glues), heat setting, adhesive welding, interlocking, application of uniform force and other bonding techniques, including methods described in U.S. Patent Application Publication US 2002/0178570 to Sogard et al. or combinations thereof. In an additional embodiment, the valve root 124 can be coupled to the first anchor frame 102 through the use of heat sealing, solvent bonding, adhesive bonding, or welding the valve root 124 to either a portion of the valve root 124 (i.e., itself) and/or the first anchor frame 102.

In an additional embodiment, the valve root 124 discussed herein could also be completely or partially constructed of natural or synthetic materials. Natural materials include, without limitation, standard porcine heart valves, equine heart valves, sheep heart valves, modified natural heart valves include those having a leaflet with a septal shelf replaced with a leaflet from another valve, and natural tissue valves wherein the cusps of the valve are formed from separate pieces of pericardial or fascia lata tissue.

Synthetic materials include, without limitation, those materials sufficiently thin and pliable so as to permit radially-collapsing of the valve leaflets for delivery by catheter to a location within a body lumen. For example, the leaflets 104 can be constructed of a biocompatible material that can be either synthetic or biologic or a combination of synthetic and biologic biocompatible material. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), polyester, polyethlylene (PE), polyethylene terephthalate (PET), silk, urethane, Rayon, Silicone, or the like. In an additional embodiment, the synthetic material can also include metals, such as stainless steel (e.g., 316L) and nitinol. These synthetic materials can be in a woven, a knit, a cast or other known physical fluid-impermeable or permeable configurations.

Additional biologic materials include, but are not limited to, autologous, allogeneic or xenograft material. These include explanted veins, pericardium, facia lata, harvested cardiac valves, bladder, vein wall, various collagen types, elastin, intestinal submucosa, and decellularized basement membrane materials, such as small intestine submucosa (SIS), amniotic tissue, or umbilical vein.

The first anchor frame 102, the sewing cushion 126, the leaflets 104 and/or the valve root 124 may also be treated and/or coated with any number of surface or material treatments. For example, suitable bioactive agents which may be incorporated with or utilized together with the present invention may be selected from silver antimicrobial agents, metallic antimicrobial materials, growth factors, cellular migration agents, cellular proliferation agents, anti-coagulant substances, stenosis inhibitors, thrombo-resistant agents, antibiotic agents, anti-tumor agents, anti-proliferative agents, growth hormones, antiviral agents, anti-angiogenic agents, angiogenic agents, cholesterol-lowering agents, vasodilating agents, agents that interfere with endogenous vasoactive mechanisms, hormones, their homologs, derivatives, fragments, pharmaceutical salts and combinations thereof.

In the various embodiments of the present invention, the most useful bioactive agents can include those that modulate thrombosis, those that encourage cellular ingrowth, through-growth, and endothelialization, those that resist infection, and those that reduce calcification. For example, coating treatments can include one or more biologically active compounds and/or materials that may promote and/or inhibit endothelial, smooth muscle, fibroblast, and/or other cellular growth onto or into the frame 102 and/or the valve root 124, including the leaflets 104. Examples of such coatings include, but are not limited to, polyglactic acid, poly-L-lactic acid, glycol-compounds, and lipid compounds. Additionally, coatings can include medications, genetic agents, chemical agents, and/or other materials and additives. In addition, agents that limit or decrease cellular proliferation can be useful. Similarly, the frame 102 and/or the valve root 124, including the leaflets 104, may be seeded and covered with cultured tissue cells (e.g., endothelial cells) derived from a either a donor or the host patient which are attached to the valve leaflets 104. The cultured tissue cells may be initially positioned to extend either partially or fully over the valve leaflets 104.

Cells can be associated with the present invention. For example, cells that have been genetically engineered to deliver bioactive proteins, such as the growth factors or antibodies mentioned herein, to the implant site can be associated with the present invention. Cells can be of human origin (autologous or allogenic) or from an animal source (xenogenic). Cells can be pre-treated with medication or pre-processed such as by sorting or encapsulation. The delivery media can be formulated as needed to maintain cell function and viability.

Thrombo-resistant agents associated with the valve may be selected from, but not limited to, heparin, heparin sulfate, hirudin, hyaluronic acid, chondroitin sulfate, dermatan sulfate, keratin sulfate, PPack (detropyenylalanine praline arginine chloromethylketone), lytic agents, including urokinase and streptokinase, their homologs, analogs, fragments, derivatives and pharmaceutical salts thereof.

Anti-coagulants can include, but are not limited to, D-Phe-Pro-Arg chloromethyl ketone, an RGD peptide-containing compound, heparain, antithrombin compounds, platelet receptor antagonists, anti-thrombin antibodies, anti-platelet receptor antibodies, aspirin, prostaglandin inhibitors, platelet inhibitors, tick antiplatelet peptides and combinations thereof.

Antibiotic agents can include, but are not limited to, penicillins, cephalosportins, vancomycins, aminoglycosides, quinolonges, polymyxins, erythromycins, tetracyclines, chloraphenicols, clindamycins, lincomycins, sulfonamides, their homologs, analogs, derivatives, pharmaceutical salts and combinations thereof.

Anti-proliferative agents for use in the present invention can include, but are not limited to, the following: paclitaxel, sirolimus, everolimus, or monoclonal antibodies capable of blocking smooth muscle cell proliferation, related compounds, derivatives, and combinations thereof.

Vascular cell growth inhibitors can include, but are not limited to, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of a an antibody and a cytotoxin.

Vascular cell growth promoters include, but are not limited to, transcriptional activators and transcriptional promoters. Anti-inflammatory agents can include, but are not limited to, dexametbasone, prednisolone, corticosterone, budesonide, estrogen, sulfasalazinemesalamne, and combinations thereof.

Although the embodiments in FIGS. 1A and 1B illustrate and describe a tri-leaflet configuration for the valve 100 of the present invention, designs employing a different number of valve leaflets are possible. For example, bi-leaflet configurations (e.g., mitral valve) are also possible.

FIG. 2 illustrates an embodiment of the valve 200 where the anchor members 206 extend from the first anchor frame 202 has just the first end 218. In other words, the anchor members 206 have a single shaft extending from the first anchor frame 202 that ends with the first end 218. As discussed herein, the anchor members 206 extend vertically over the surface 208 defining the opening 210 through the first anchor frame 202 when the cardiac valve 200 is in its fully deployed configuration. For example, in one embodiment the anchoring members 206 extend parallel with a common axis 212 that is perpendicular to a common plane 214 extending through the first anchor frame 202. In an additional embodiment, the anchoring members 206 can extend at an acute angle 216 to the common axis 212 that is perpendicular to the common plane 214 extending through the first anchor frame 202.

As discussed herein, the first end 218 of the anchor members 206 each have a size and configuration that are adapted to both penetrate tissue (e.g., the fibrous tissue that surrounds cardiac valves) and to anchor the cardiac valve 200 to the tissue. In addition, a variety of structures and configurations of the anchor members 206 are available for anchoring the cardiac valve 200 to the tissue. For example, the first end 218 can include a barb for penetrating and anchoring the cardiac valve 200 to the tissue.

In an additional embodiment, the anchor members 206 can have material characteristics that allow the cardiac valve 200 to be secured to the cardiac tissue, as discussed herein. For example, the anchor members 206 can be imparted with a driving force to move from a first predetermined shape to a second predetermined shape to anchor the cardiac valve 200 to tissues. In one embodiment, this movement can be on account of the first end 218 of the anchor members 106 being restrained or held in the first predetermined position under tension. When no longer restrained, the first end 218 of the anchor members 206 move back towards the second predetermined position. In the present example, the first end 218 of the anchor members 206 move in a radial direction toward the perimeter of the first anchor frame 202. In one embodiment, the first end 218 are held in tension due to the presence of a deployment member that can be radially compressing the first end 218 of the anchor members 206, as will be discussed more fully herein.

The anchor members 206 can also have a variety of shapes that allow for the first end 218 to be held under tension. For example, the anchor members 206 can be held under tension so as to have an overall linear-shaped configuration. After removing the restraint, the first end 218 moves radially to anchor the cardiac valve 200 to the cardiac tissue. For example, the first end 218 of the anchor members 206 can move radially from the opening 210 to take on a J-shaped configuration, thereby drawing and securing the valve 200 into the cardiac tissue surrounding native cardiac valve. Other shapes and configurations are also possible. The first end 218 of the anchor member 206 can also include a barb, as discussed herein.

The anchor members 206 can be formed from a wide variety of materials and can display the same dimensions relative the first anchor frame 202 (e.g., extending of the surface 208 of the first anchor frame 202 by the predetermined distance), as discussed herein. In addition, while the anchor members 206 are shown positioned completely around the first anchor frame 202, other placement configurations for the anchor members 206 are possible, as discussed herein.

Figure 3:
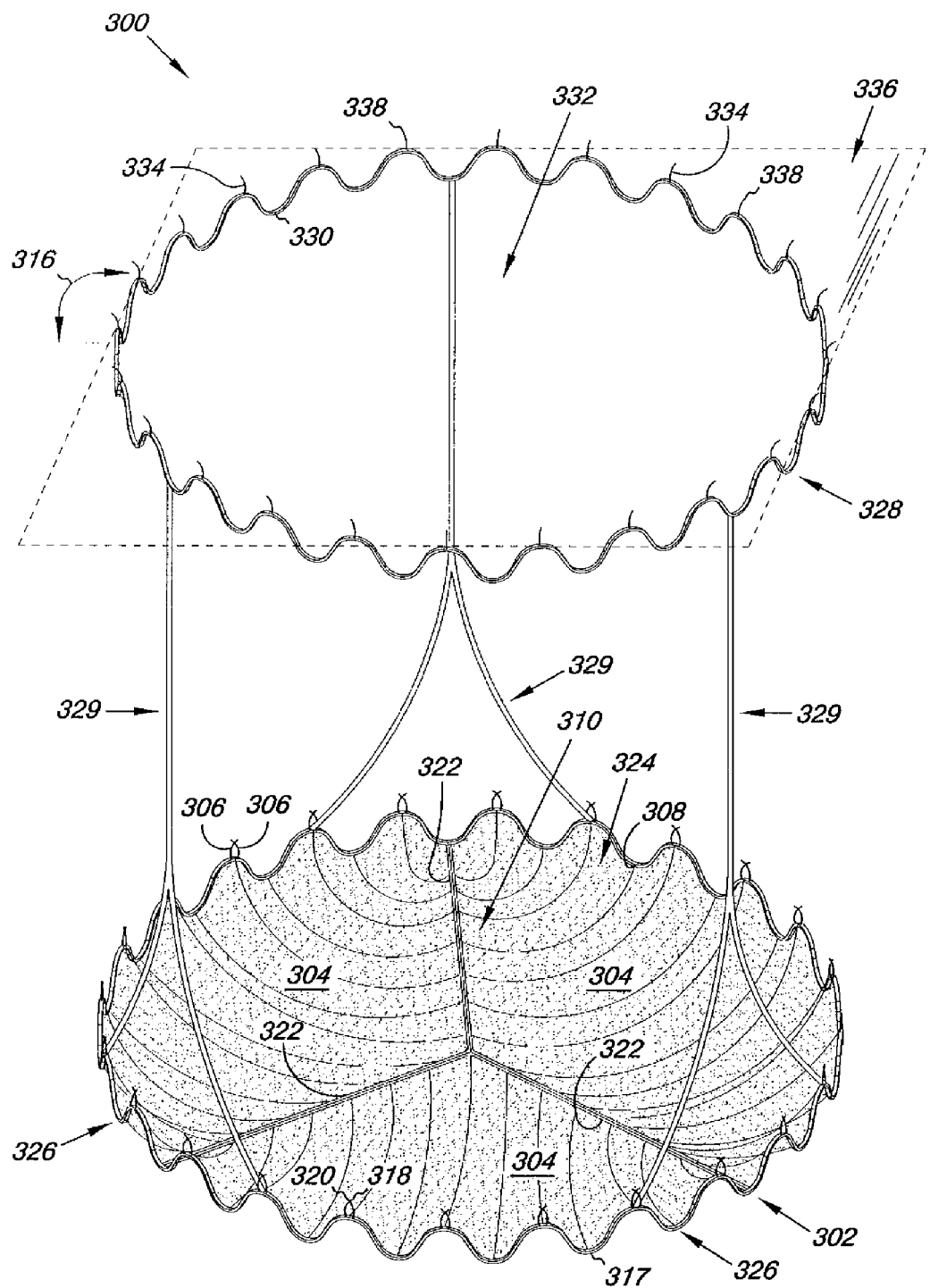
FIG. 3 illustrates an embodiment of a valve.

FIG. 3 illustrates an additional embodiment of the cardiac valve 300. The cardiac valve 300 includes the first anchor frame 302, two or more leaflets 304, and two or more anchor members 306, as discussed herein. In addition, the cardiac valve 300 further includes a second anchor frame 328 connected to the first anchor frame 302 through struts 329 extending between the first anchor frame 302 and the second anchor frame 328. In one embodiment, the leaflets 304 can be coupled to the struts 329 and the first anchor frame 302. In addition, the struts 329 can allow for tension to be developed between the first and second anchor frames 302 and 328 when the cardiac valve 300 is implanted, as will be more fully discussed herein.

The second anchor frame 328 includes a surface 330 defining an opening 332 through the second anchor frame 328. The second anchor frame 328 can optionally include leaflets, as discussed herein, for unidirectional flow of the liquid through the opening 332.

The second anchor frame 328 further includes two or more anchor members 334 extending from the surface 330 of the second anchor frame 328. As illustrated, the anchor members 334 extend at an acute angle 316 to the common plane 336 extending through the second anchor frame 328 when the cardiac valve 300 is in its fully deployed configuration. In an additional embodiment, the anchoring members 334 can extend perpendicular to the common axis 312 that is parallel to the common plane 336 extending through the second anchor frame 328 (i.e., the anchoring members 334 can be parallel with the common plane 336).

The second anchor frame 328 can have a variety of configurations and can be formed from a variety of materials, as were discussed herein for the first anchor frame 302. In addition, the second anchor frame 328 can be configured to be implanted in an artery or vein, while the first anchor frame 302 resides in the fibrous ring surrounding the orifice of the cardiac valve that is being augmented or replaced with the cardiac valve 300. For example, the second anchor frame 328 can be configured to be implanted in the aorta, while the first anchor frame 302 resides in the fibrous ring surrounding the orifice of the aortic valve. Other locations are possible.

In addition, the anchor members 334 can also be joined and/or formed from the same materials and/or the frame members of the second anchor frame 328, as discussed herein for the first anchor frame 302. As illustrated in FIG. 3, the anchor members 334 can each include at least a first end 338, where the anchor members 334 have a size and configuration that are adapted to both embed into the tissue (e.g., the artery or vein) and to help anchor the cardiac valve 300.

A variety of structures and configurations of the anchor members 334 are available for anchoring the cardiac valve 300 to the tissue. For example, the first end 338 can include a barb for penetrating and anchoring the cardiac valve 300. In addition, while the anchor members 334 are shown positioned completely around the second anchor frame 328, other placement configurations for the anchor members 334 are possible such as those discussed herein for the anchor members 306.

In an additional embodiment, the anchor members 334 can have dimensional and material characteristics that allow the cardiac valve 300 to be secured to the cardiac tissue, as discussed herein for anchor members 306. For example, the anchor members 334 can be constructed and shaped in such a way that the first ends 338 of the anchor members 334 have a driving force to move from a first predetermined shape to a second predetermined shape to anchor the cardiac valve 300, as discussed herein for anchor members 306. In one embodiment, this movement can be on account of the first ends 338 of the anchor members 334 being restrained or held in the first predetermined position under tension. When no longer restrained, the first ends 338 of the anchor members 334 move back towards the second predetermined position. An embodiment of the second predetermined position is illustrated in FIG. 3. In one embodiment, the first second ends 338 are held in tension due to the presence of a deployment member that can be removed from the first ends 338 and 120, as will be discussed more fully herein.

The anchor members 334 can also have a variety of shapes that allow for the first ends 338 to be held under tension, as will be discussed more fully herein. For example, the anchor members 334 can be held under tension so as to have an overall linear configuration that changes to have a hooked end portion (i.e., a J-shaped end) after removing the restraint. Other shapes and configurations are also possible.

As illustrated, the cardiac valve 300 includes struts 329 that connect the second anchor frame 328 to the first anchor frame 302. In one embodiment, the struts 329 can generally have a circular cross section and be of substantially uniform diameter throughout their entire extent. Alternatively, the struts 329 can have a rectangular profile. As will be appreciated, other cross-sectional shapes are also possible (e.g., square, triangular, oval, etc.). In one embodiment, the cross-sectional shape of the struts 329 is the same as the cross-sectional shape of the frame members of the first and second anchor frames 302 and 328.

FIG. 3 provides an illustration in which the struts 329 extend linearly between the valve 300 and the second anchor frame 328. As will be appreciated, the struts 329 can have a number of different cross-sectional and elongate configurations. For example, the struts 329 may have a rectangular profile and extend between the valve 300 and the second anchor frame 328 in a serpentine shape. In one embodiment, the cross-sectional shape and elongate configurations of the struts 329 can allow for additional contact area to be provided between the struts 329 and the tissue of the implant site. For example, the rectangular cross-sectional shape and the serpentine elongate configuration can allow for aligning and confining the patients existing cardiac valve leaflets in an open position during and after the implantation of the cardiac valve 300.

As illustrated in FIG. 3, the struts 329 can be integral to the first and second anchor frames 302 and 328. Alternatively, the struts 329 can be separately coupled to the first and second anchor frames 302 and 328 through the coupling processes described herein or that are known. In addition, the struts 329 can allow for tension to be developed between the first and second anchor frames 302 and 328 when the cardiac valve 300 is implanted, as will be more fully discussed herein.

In an additional embodiment, the struts 329 can be configured to extend into the opening 310 of the first anchor frame 302. This allows, besides other things, for the struts 329 to be clear of the vertically oriented anchoring members 306. The struts 329 can then arch back radially to couple to the second anchor frame 328.

The struts 329 may be formed of, for example, any material which is non-corrosive, fatigue resistant, and biocompatible. Examples of such materials have been provided herein in connection with the first and second anchor frames 302 and 328. As will be appreciated, the first and second anchor frames 302 and 328 and the struts 329 can be formed from in a single piece (e.g., through a laser or water cutting process) of tubular material. Alternatively, each of the first and second anchor frames 302 and 328 and the struts 329 could be formed separately and then coupled as described herein. The edges of the resulting structure can then be polished and contoured.

In addition to joining the first and second anchor frames 302 and 328, the configuration of the struts 329 also allow for additional options in coupling the leaflets 304 to the valve 300. For example, at least part of the leaflets 304, as discussed herein, can be coupled to the struts 329 and the first anchor frame 302 to provide the reversibly sealable opening 322 for unidirectional flow of a liquid through the valve 300. As will be appreciated, the valve root 324 derived from the xenographic donor can also be coupled to at least part of both the struts 329 and the first anchor frame 302.

The valve root 324 can be mounted to the first anchor frame 302 and the struts 329 in a variety of ways. For example, the first anchor frame 302 and the struts 329 can both include a least a portion of the sewing cushion 326 to which the valve root 324 can be attached. The valve root 324 can then be stitched to the sewing cushion 326, as discussed herein. Other coupling techniques, as discussed herein, could also be used. In an additional embodiment, the valve root 324 can be coupled to the first anchor frame 302 and/or the struts 329 through the use of heat sealing, solvent bonding, adhesive bonding, or welding the valve root 324 to either a portion of the valve root 324 (i.e., itself) and/or the first anchor frame 302 and the struts 329.

Figure 4B:
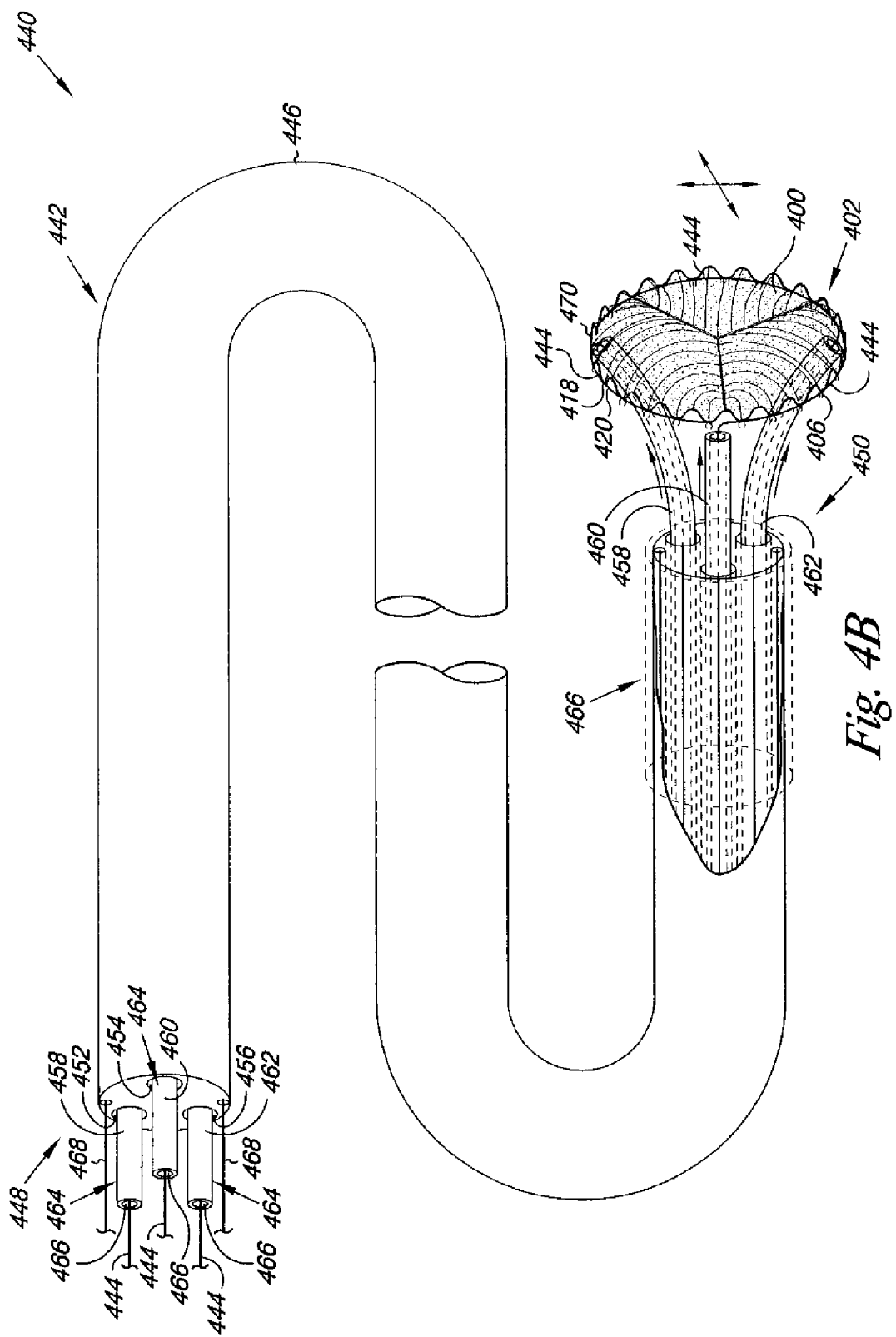
Figure 4C:
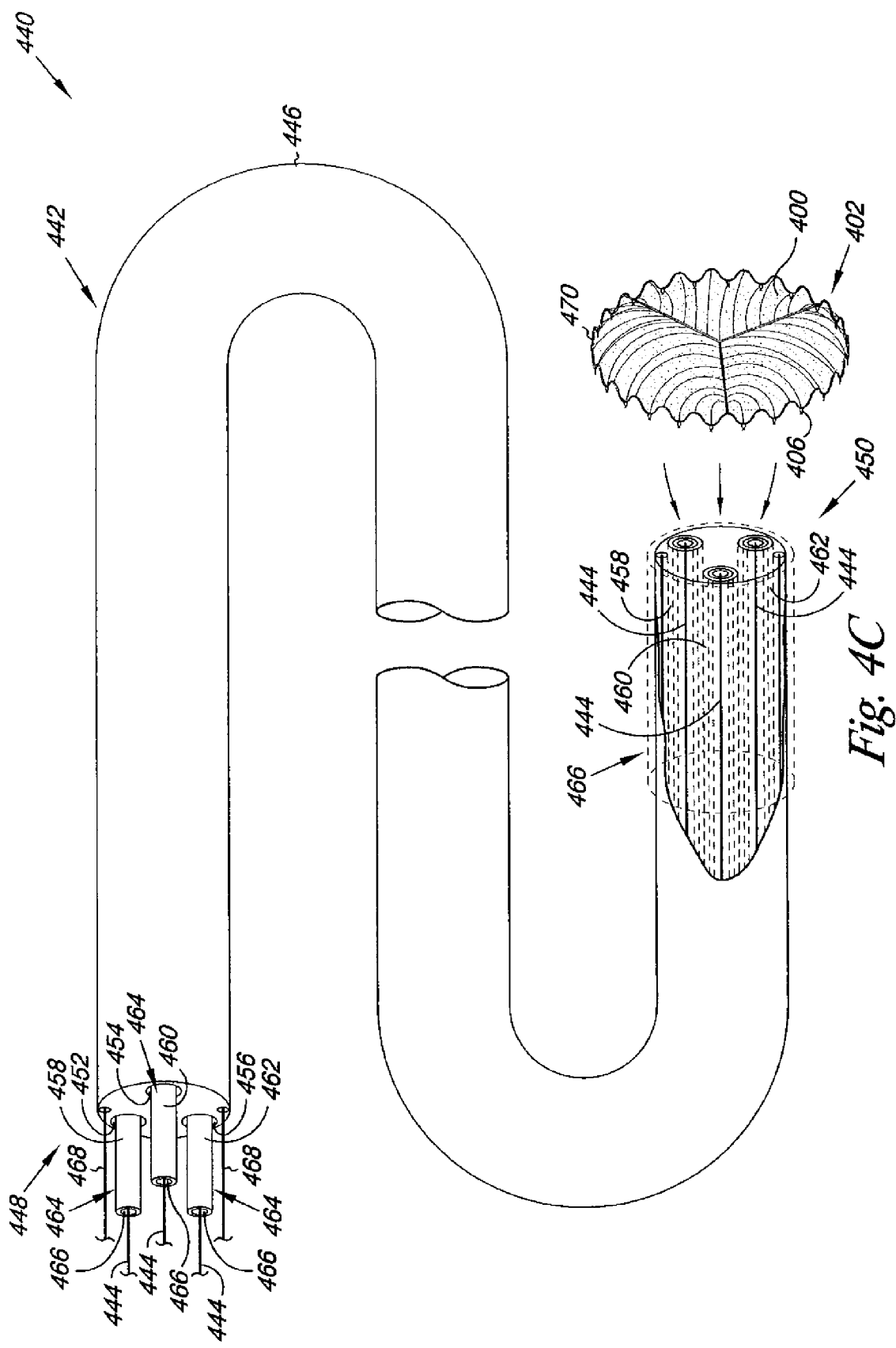

FIGS. 4A-4C illustrate one embodiment of a system 440. System 440 includes valve 400, as described herein, releasably joined to a delivery catheter 442. FIG. 4A illustrates an embodiment in which the valve 400 in an undeployed configuration is releasably joined to a delivery catheter 442. FIG. 4B illustrates an embodiment in which the valve 400 is in its fully deployed configuration while being releasably joined to a delivery catheter 442. Finally, FIG. 4C illustrates an embodiment in which the valve 400 in its fully deployed configuration has been released from the delivery catheter 442. In one embodiment, the valve 400 can be reversibly joined to the delivery catheter 442 through the use of one or more deployment members 444, as will be discussed below.

In the example illustrated in FIGS. 4A-4C, the delivery catheter 442 includes an elongate body 446 having a proximal end 448 and a distal end 450, where valve 400 can be located between the proximal end 448 and distal end 450. The delivery catheter 442 further includes a first delivery lumen 452, a second delivery lumen 454, and a third delivery lumen 456 extending from the proximal end 448 towards the distal end 450 of the delivery catheter 442.

The delivery catheter 442 also includes a first placement guide 458, a second placement guide 460, and a third placement guide 462. Each of the first, second, and third placement guides 458, 460, and 462 has an elongate body 464 with a lumen 466 extending there through. As illustrated in FIGS. 4A-4C, each of the first, second, and third placement guides 458, 460, and 462 are positioned and can travel longitudinally within their respective delivery lumens 452, 454, and 456. In one embodiment, this allows at least a portion of the first, second, and third placement guides 458, 460, and 462 to extend beyond the distal end 450 of the delivery catheter 442.

The delivery catheter 442 also has deployment members 444 that extend through the lumens of the first, second, and third placement guides 458, 460, and 462. In one embodiment, the deployment members 444 extend beyond the first, second, and third placement guides 458, 460, and 462 and are releaseably positioned adjacent the anchoring members 406. For example, the deployment members 444 can be releaseably positioned so as to constrain the first end 418 and the second end 420 of the anchor members 406 in the first predetermined relationship. The deployment members 444 can then be retracted from their positions relative the anchoring members 406, whereupon the first end 418 and the second end 420 of the anchor members 406 to move to the second predetermined relationship.

Referring now to FIG. 4A, there is illustrated the system 440 with the valve 400 in an undeployed configuration releasably coupled to the delivery catheter 442. In one embodiment, the valve 400 can be releasably coupled to the delivery catheter 442 through the deployment members 444. For example, the deployment members 444 can extend from one or more of the first, second, and third placement guides 458, 460, and 462 to contact the anchor members 406. As discussed above, the anchor members 406 are constructed and shaped in such a way that the first and second ends 418 and 420 of the anchor members 106 have a driving force to move from a first predetermined shape to a second predetermined shape to anchor the cardiac valve 400 to tissues. In one embodiment, this movement can be on account of the first and second ends 418 and 420 of the anchor members 406 being restrained or held in the first predetermined position under tension by the presence of the deployment members 444.

In addition to holding the first and second ends 418 and 420 of the anchor members 406 in the first predetermined position under tension, the deployment members 444 also releasably couples the valve 400 to the delivery catheter 442. In the embodiment illustrated in FIG. 4A the valve 400 has been coupled to the delivery catheter 442 in its undeployed configuration. In one embodiment, in its undeployed configuration the valve 400 has been radially compressed (e.g., the first anchor frame 402 has been radially compressed) to reduce the size of the valve 400. As illustrated in FIG. 4A, the valve 400 in its undeployed configuration can further be held in place (e.g., constrained) by the presence of a retractable sheath 466 positioned adjacent the distal end 450 of the delivery catheter 442.

In one embodiment, the retractable sheath 466 can be positioned over at least a portion of the elongate body 446, where the retractable sheath 466 can move longitudinally along the elongate body 446. The valve 400 can be positioned at least partially within the retractable sheath 466, where the retractable sheath 466 moves along the elongate body 446 to help deploy the valve 400. In one embodiment, a retraction system 468 can be used to help move the retractable sheath 466, where the system 468 includes one or more wires coupled to the retractable sheath 466. The wires of the retraction system 468 can longitudinally extend at least partially through lumens in the elongate body 446. Wires of the retraction system 468 can then be used to retract the retractable sheath 466 in deploying valve 400.

FIG. 4B illustrates an embodiment in which the valve 400 is being expanded into its fully deployed configuration while still being releasably joined to a delivery catheter 442. As illustrated, the retraction system 468 has been used to retract the retractable sheath 466 in deploying valve 400. The first, second, and third placement guides 458, 460, and 462 have also been extended from the distal end 450 of the delivery catheter 442. As compared to FIG. 4A, the first anchor frame 402 illustrated in FIG. 4B has expanded from a first predetermined configuration (e.g., the undeployed configuration) to the fully deployed configuration as the first, second, and third placement guides 458, 460, and 462 extend beyond the distal end 450 of the delivery catheter 442.

As illustrated, the first, second, and third placement guides 458, 460, and 462 can connect to the cardiac valve 400 through the separate portions of the deployment member 444 at points symmetrically positioned around the first anchor frame 402 of the cardiac valve 400. Other non-symmetrical connection points for the placement guides 458, 460, and 462 and the first anchor frame 402 of the cardiac valve 400 are also possible.

In one embodiment, as the placement guides 458, 460, and 462 are extended from the delivery catheter 442 they flare radially as the valve 400 begins to move from its undeployed configuration to its deployed configuration. As illustrated, in one embodiment the first, second, and third placement guides 458, 460, and 462 are positioned adjacent the anchor members 406 so as not to interfere with the anchor members 406 as they are embedded into, for example, the cardiac tissue surrounding a cardiac valve.

FIG. 4C illustrates an embodiment in which the valve 400 in its fully deployed configuration has been released from the delivery catheter 442. In one embodiment, releasing the valve 400 in its fully deployed configuration can be accomplished by retracting the portions of the one or more deployment members 444 from being in contact with the anchor members 406. In one embodiment, this can be accomplished by pulling on the deployment members 444 to release the cardiac valve 400 from the first, second, and third placement guides 458, 460, and 462 and the delivery catheter 442. Upon removing the deployment members 444, the anchor members 406 can then move from a first predetermined shape (as illustrated in FIGS. 4A and 4B) to a second predetermined shape (as illustrated in FIG. 4C) to anchor the cardiac valve 400 to tissues.

In one embodiment, the deployment members 444 can have a variety of configurations and be constructed of a variety of materials. For example, the deployment members 444 can have a wire configuration with a size sufficiently large to hold the anchor members 406 in the first predetermined shape. Examples of different configurations for cross-sectional shapes of the wire can include, but are not limited to, round, oval, square, triangular and other shape as are known. Examples of suitable materials include medical grade stainless steel (e.g., 316L), titanium, cobalt alloys, alginate, or combinations thereof.

In an additional embodiment, the cardiac valve 400 can further include a sealing material 470 positioned between the first anchor frame 406 and the deployment member 444. In one embodiment, upon removing the deployment member 444 to anchor the cardiac valve 400 to the tissue the sealing material 470 can swell due the presence of liquid to occupy volume between the first anchor frame 402 and the tissue on which the valve has been implanted so as to prevent leakage of the liquid outside of the opening 410 of the cardiac valve 400. In alternative embodiment, the sealing material 470 can have a microcoil configuration. Examples of microcoil structures include, but are not limited to, those sold by the Micrus Corporation of Sunnyvale Calif. under the trade designator "ACT MicroCoil."

A variety of suitable materials for the sealing material 470 are possible. For example, the sealing material 470 can be selected from the general class of materials that include polysaccharides, proteins, and biocompatible gels. Specific examples of these polymeric materials can include, but are not limited to, those derived from poly(ethylene oxide) (PEO), poly(ethylene glycol) (PEG), poly(vinyl alcohol) (PVA), poly(vinylpyrrolidone) (PVP), poly(ethyloxazoline) (PEOX) polyaminoacids, pseudopolyamino acids, and polyethyloxazoline, as well as copolymers of these with each other or other water soluble polymers or water insoluble polymers. Examples of the polysaccharide include those derived from alginate, hyaluronic acid, chondroitin sulfate, dextran, dextran sulfate, heparin, heparin sulfate, heparan sulfate, chitosan, gellan gum, xanthan gum, guar gum, water soluble cellulose derivatives, and carrageenan. Examples of proteins include those derived from gelatin, collagen, elastin, zein, and albumin, whether produced from natural or recombinant sources.

As will be appreciated, the sealing material 470 can be presented on the first anchor frame 402 in such a way as to expand in volume upon contacting the liquid. In one embodiment, in order to inhibit the sealing material 470 from swelling prior to implanting the valve 400, the sealing material 470 can be positioned between the anchor frame 402 and the deployment members 444 so as to keep the sealing material 470 from contacting liquid until the deployment members 444 are removed from the valve 400.

Figure 5A:
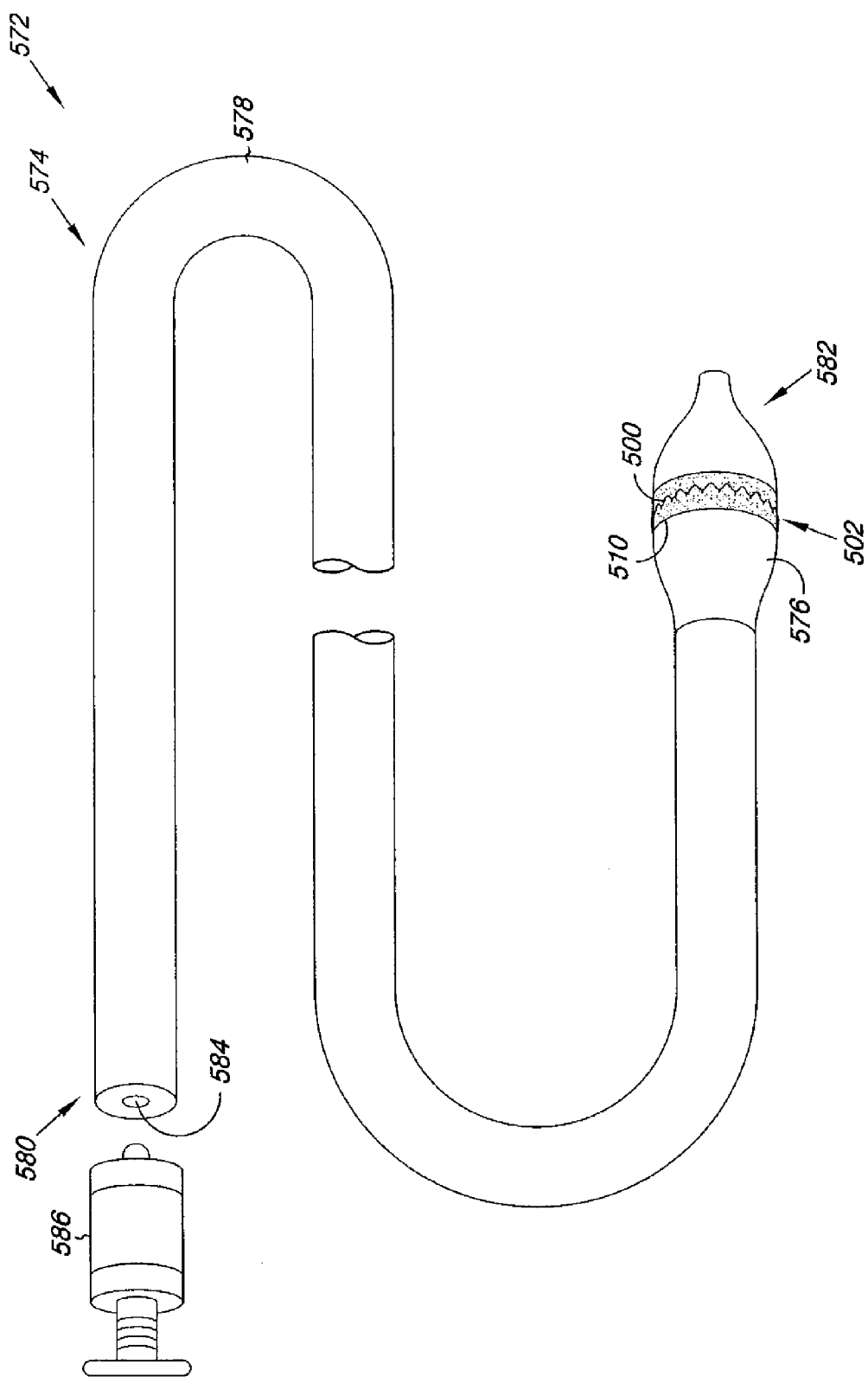
FIGS. 5A-5C illustrate an embodiment of a system that includes a valve.
Figure 5B:
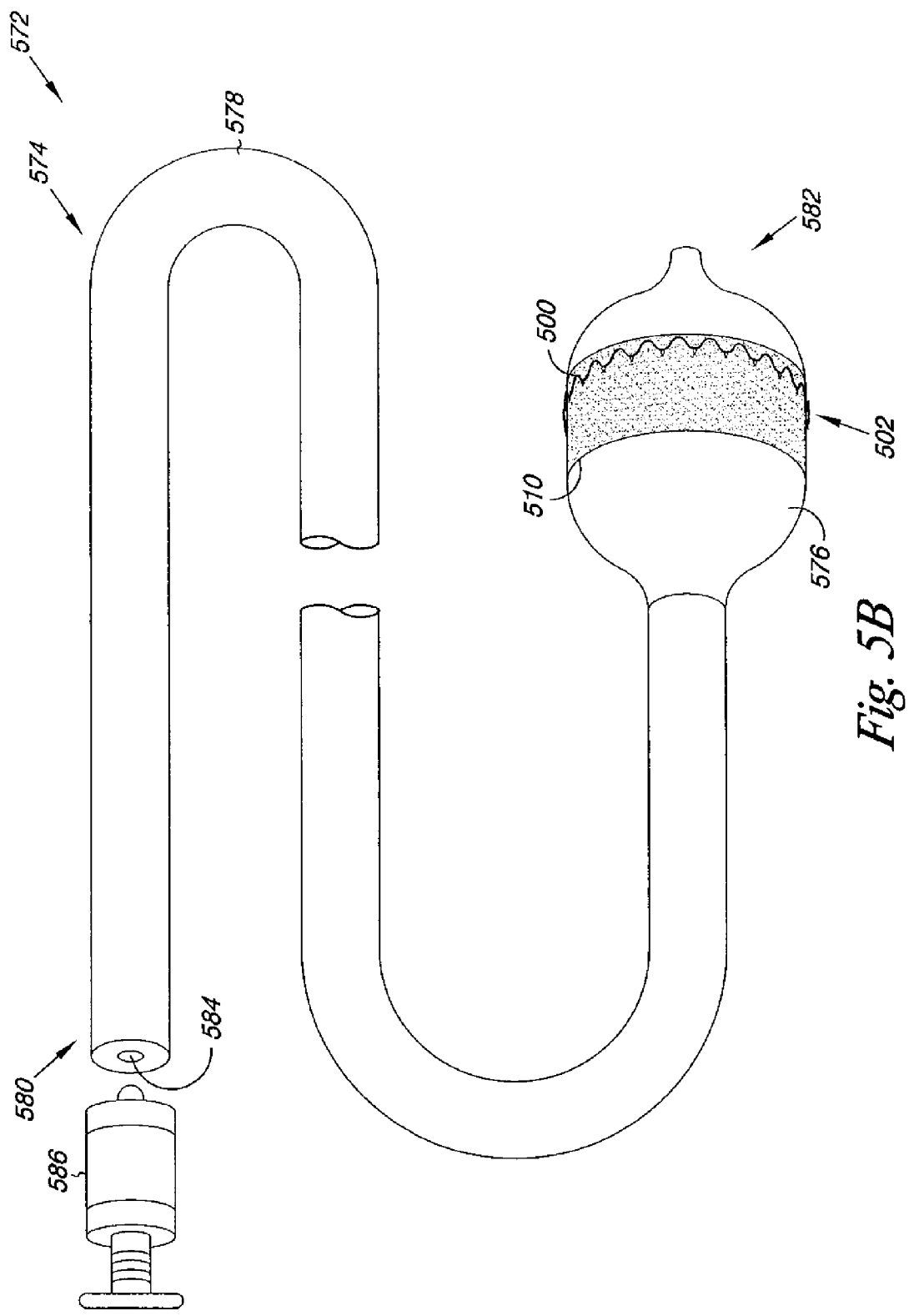
Figure 5C:
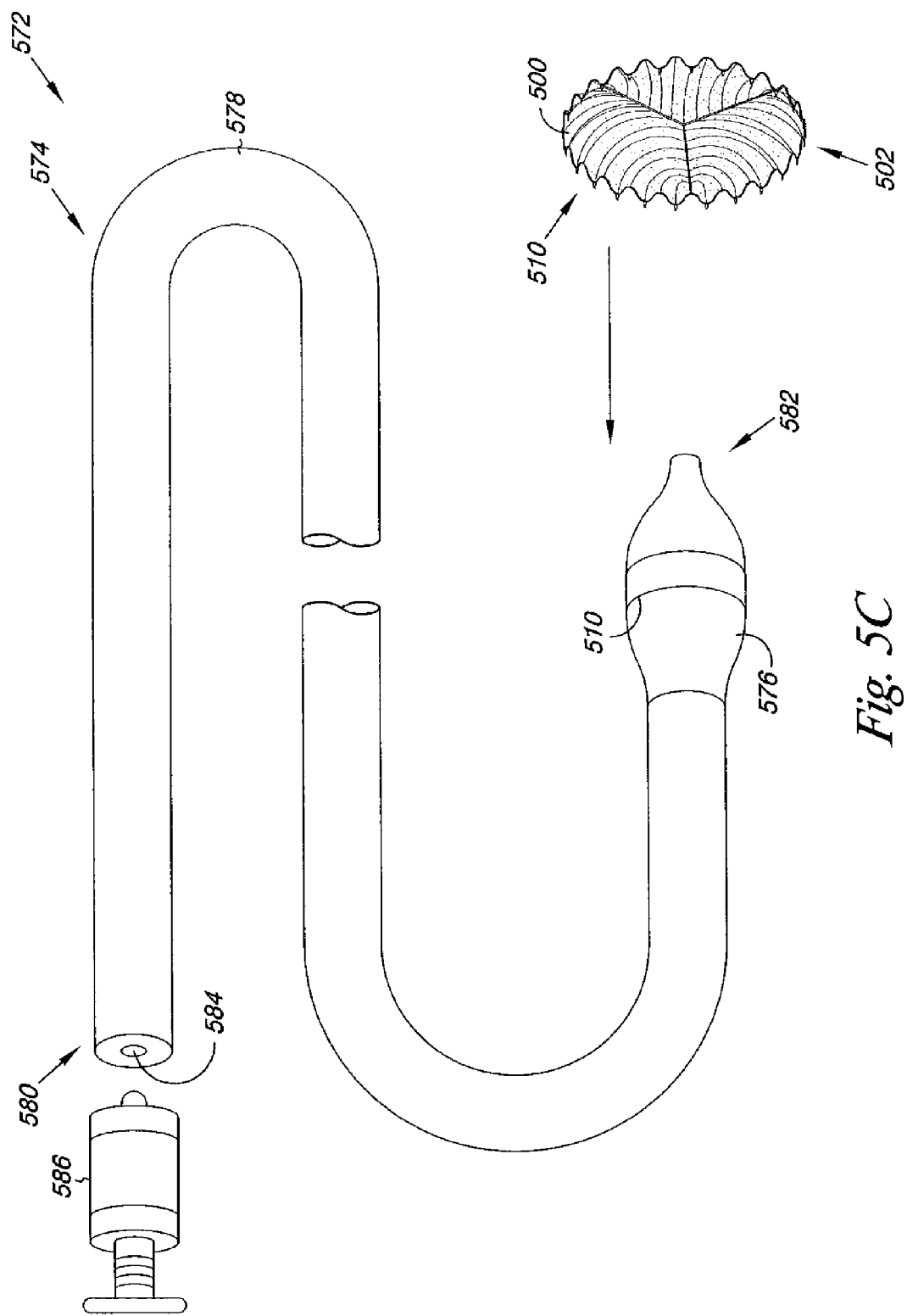

FIGS. 5A-5C illustrate an additional embodiment of a system 572. System 572 includes valve 500, as described herein, releasably joined to a delivery catheter 574. FIG. 5A illustrates an embodiment in which the valve 500 in an undeployed configuration is releasably joined to a delivery catheter 574. FIG. 5B illustrates an embodiment in which the valve 500 is in its fully deployed configuration while being releasably joined to a delivery catheter 574. Finally, FIG. 5C illustrates an embodiment in which the valve 500 in its fully deployed configuration has been released from the delivery catheter 574. In one embodiment, the valve 500 can be reversibly joined to the delivery catheter 574 through the use of a first inflatable balloon 576, as will be discussed below.

In the example illustrated in FIGS. 5A-5C, the delivery catheter 574 includes an elongate body 578 having a proximal end 580 and a distal end 582. The delivery catheter 574 further includes the first inflatable balloon 576 positioned adjacent the distal end 582, and a first inflatable lumen 584 longitudinally extending in the elongate body 578 of the catheter 574 from within the first inflatable balloon 576 to the distal end 582. As will be appreciated, an inflating apparatus 586 can be used to inflated and deflate the first inflatable balloon 576.

In the present example, the first inflatable balloon 576 can be at least partially positioned within the opening 510 of the first anchor frame 502. In one embodiment, the first inflatable balloon 576 can be inflated to expand the first anchor frame 502 of the cardiac valve 500 from a first predetermined configuration to the fully deployed configuration.

In an additional embodiment, the first inflatable balloon 576 can be used to help align the expanded cardiac valve 500 and the fibrous tissue that surrounds cardiac valve prior to the cardiac valve 500 being implanted. For example, the first inflatable balloon 576 can be sufficiently long that the first inflatable balloon 576 with the undeployed cardiac valve 500 (as illustrated in FIG. 5A) can be passed through the native cardiac valve to position the cardiac valve 500 adjacent its implant site while still having a portion of the balloon adjacent the native cardiac valve. The first inflatable balloon 576 can then be inflated to both expand the cardiac valve 500 to its undeployed configuration and to contact the native cardiac valve. In this way, the first inflatable balloon 576 has aligned the expanded cardiac valve with its vertically projecting anchoring members 506 with the fibrous tissue surrounding the native cardiac valve. While the first inflatable balloon 576 is still inflated, the delivery catheter 574 can then be pulled so as to embed and anchor the anchoring members 506 into the fibrous tissue surrounding the native cardiac valve. The first inflatable balloon 576 can then be deflated and removed leaving the cardiac valve 500 in its implant location.

Figure 6A:
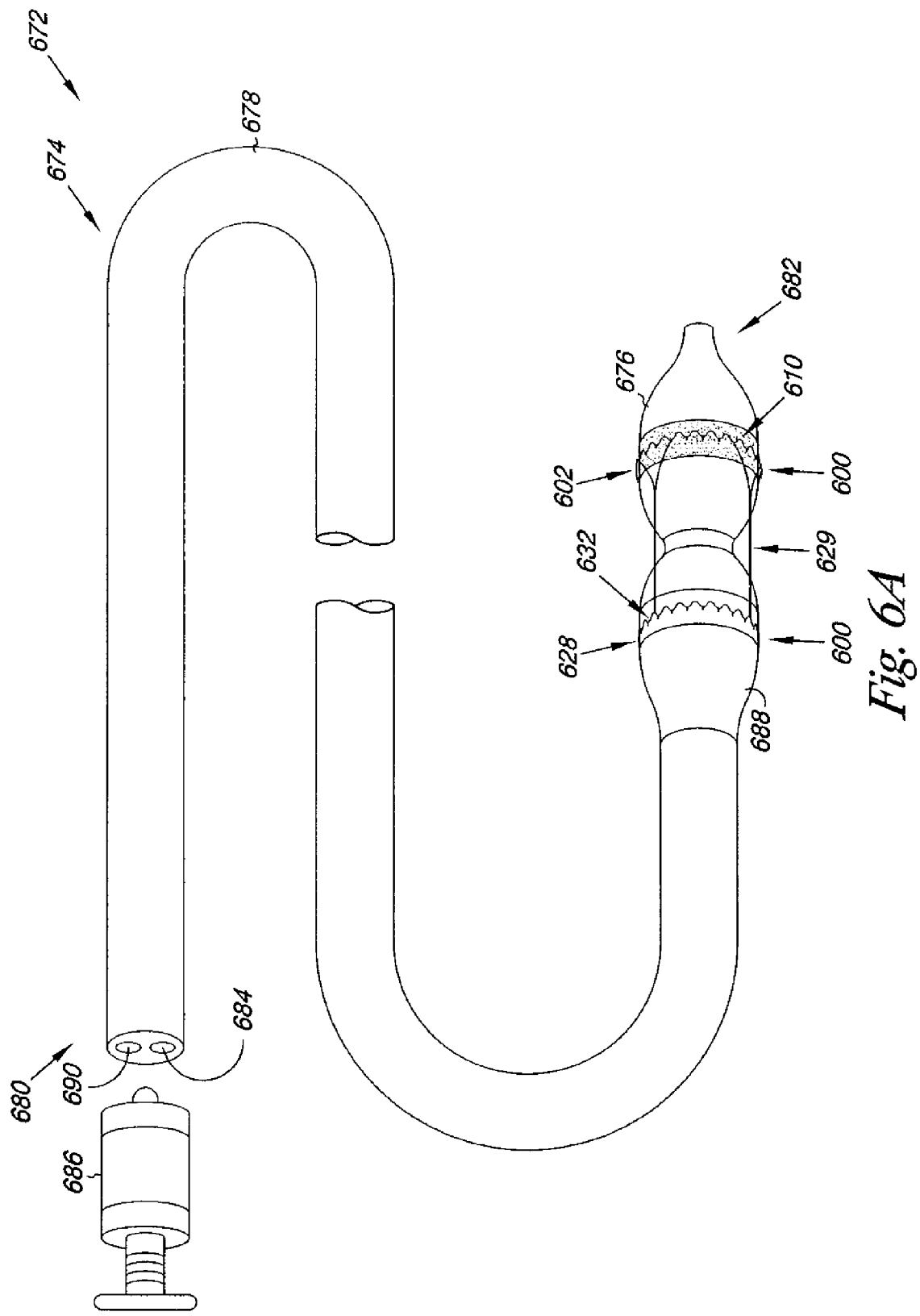
FIGS. 6A-6D illustrate an embodiment of a system that includes a valve.
Figure 6B:
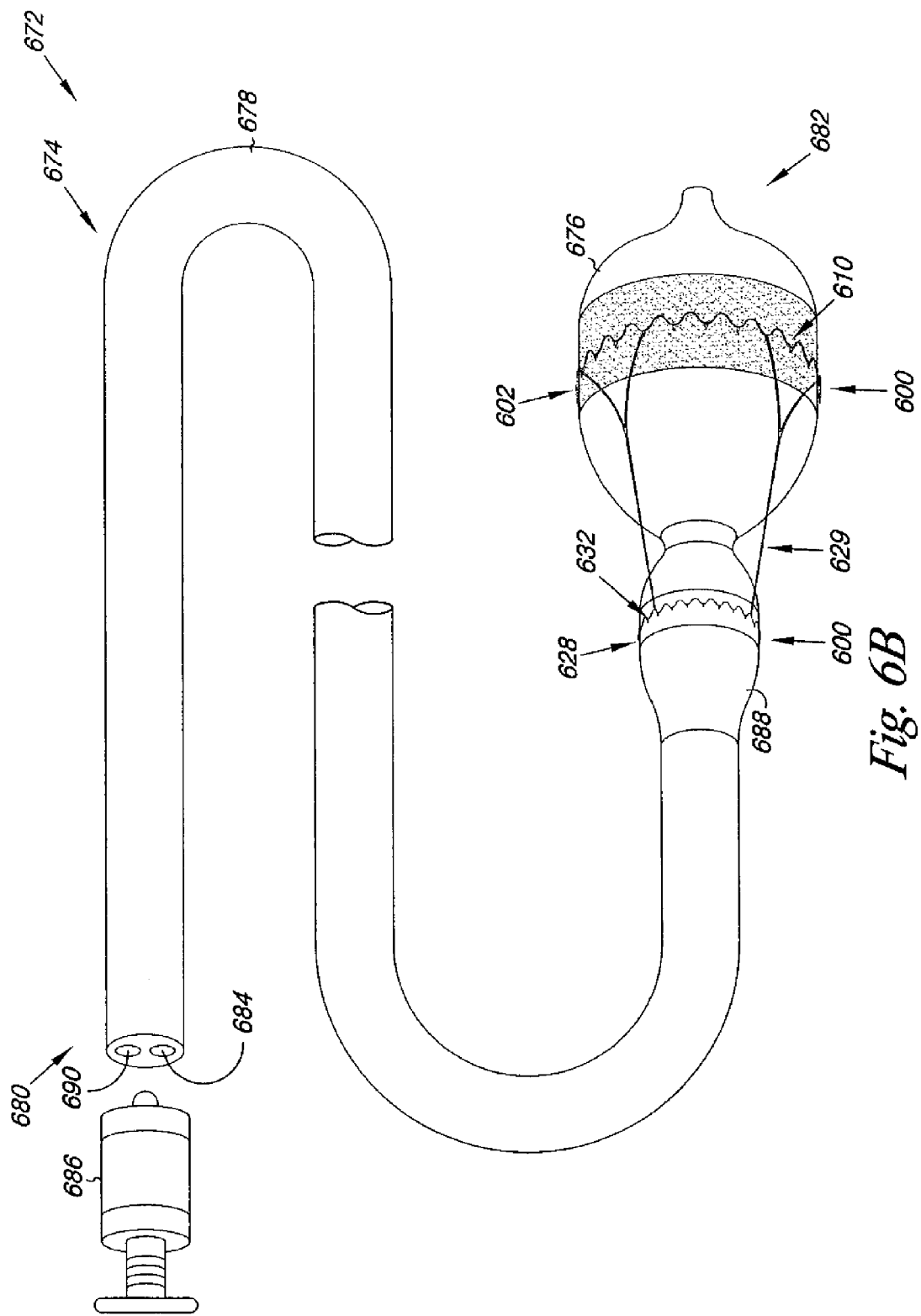
Figure 6C:
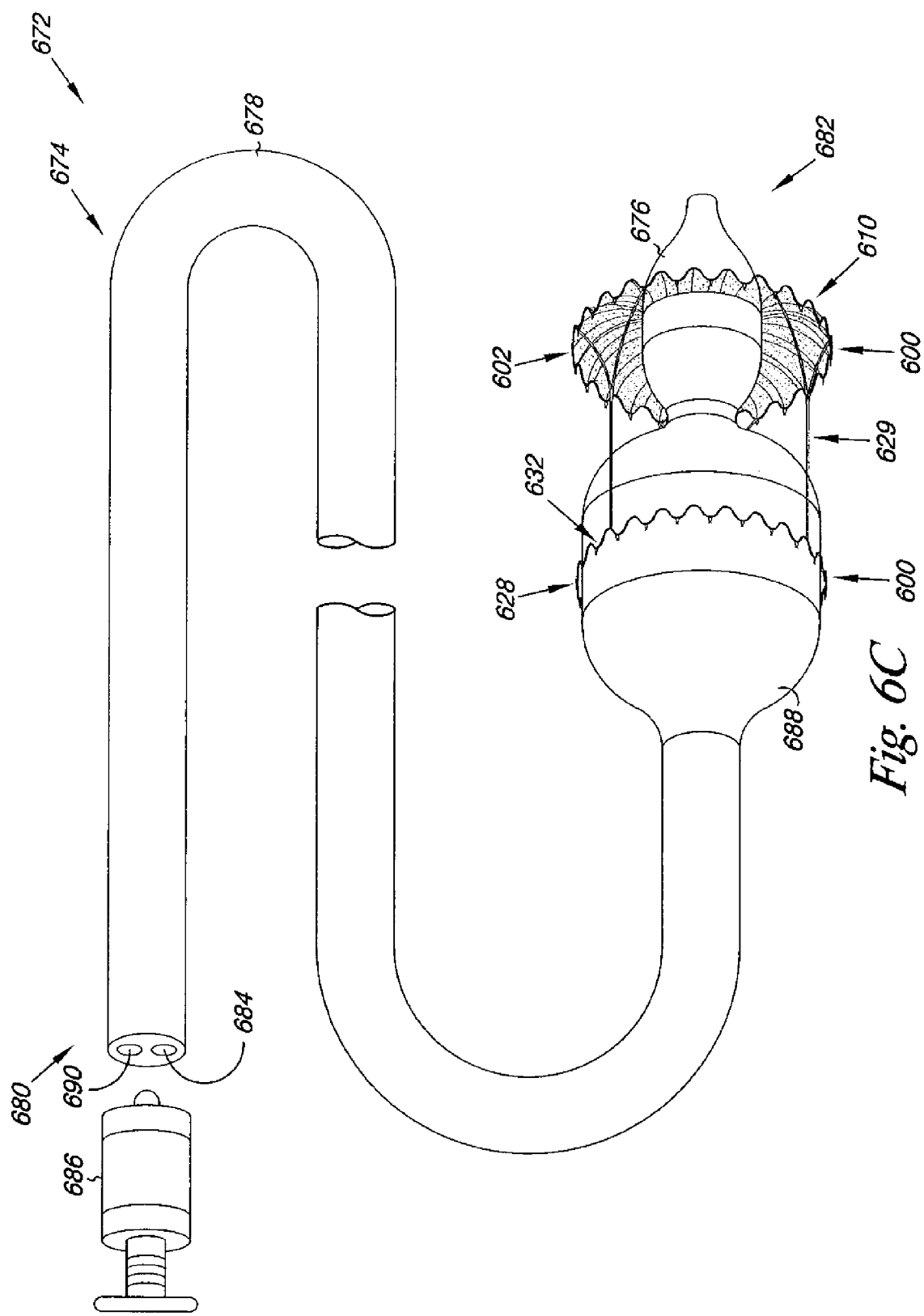
Figure 6D:
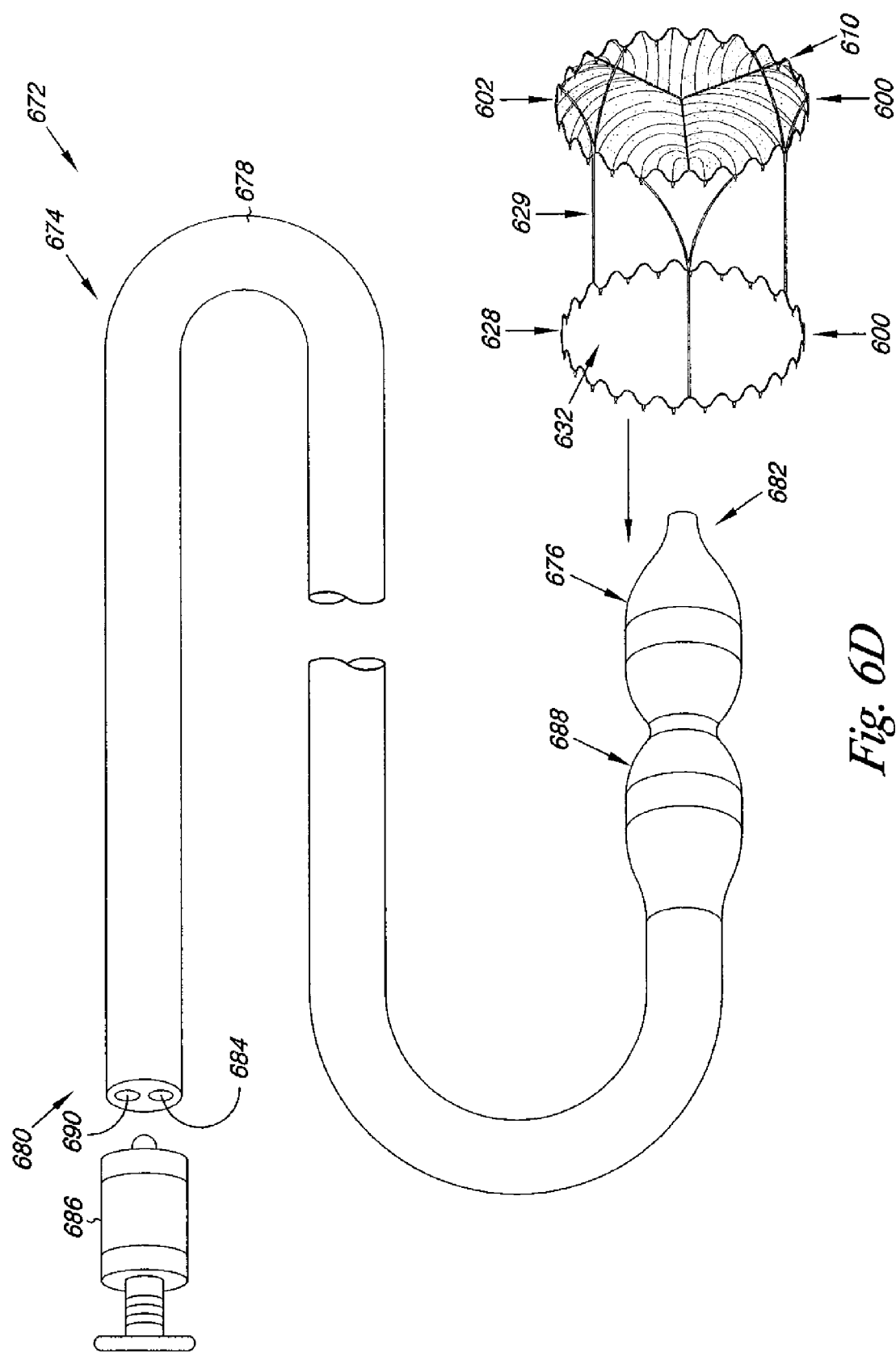

FIGS. 6A-6D illustrate an additional embodiment of the system 672. As illustrated, the system 672 includes valve 600, as described herein, releasably joined to a delivery catheter 674. FIG. 6A illustrates an embodiment in which the valve 600 in an undeployed configuration is releasably joined to a delivery catheter 674. FIG. 6B illustrates an embodiment in which the first anchor frame 602 of the valve 600 is in its fully deployed configuration while being releasably joined to a delivery catheter 674. FIG. 6C illustrates an embodiment in which the second anchor frame 628 of the valve 600 is in its fully deployed configuration while being releasably joined to a delivery catheter 674. Finally, FIG. 6D illustrates an embodiment in which the valve 600 in its fully deployed configuration has been released from the delivery catheter 674. In one embodiment, the valve 600 can be reversibly joined to the delivery catheter 674 through the use of the first inflatable balloon 676 and a second inflatable balloon 688, as will be discussed below.

In the example illustrated in FIGS. 6A-6D, the delivery catheter 674 includes the elongate body 678 having a proximal end 680 and a distal end 682. The delivery catheter 674 further includes the first inflatable balloon 676 positioned adjacent the distal end 682, and the first inflatable lumen 684 longitudinally extending in the elongate body 678 of the catheter 674 from within the first inflatable balloon 676 to the distal end 682. The delivery catheter 674 also the second inflatable balloon 688 positioned proximal to the first inflatable balloon 676, where a second inflatable lumen 690 longitudinally extends in the elongate body 678 of the catheter 674 from within the second inflatable balloon 688 to the distal end 682. As will be appreciated, an inflating apparatus 686 can be used to inflated and deflate the first and second inflatable balloons 676 and 688 either simultaneously or separately.

In the present example, the first inflatable balloon 676 can be at least partially positioned within the opening 610 of the first anchor frame 602. Similarly, the second inflatable balloon 688 can be at least partially positioned within the opening 632 of the second anchor frame 628. In one embodiment, the first and second inflatable balloons 676 and 688 can be inflated to expand the first anchor frame 602 and the second anchor frame 628, respectively, of the cardiac valve 600 from a first predetermined configuration to the fully deployed configuration.

In an additional embodiment, the first inflatable balloon 676 can be used to help align the expanded first anchor frame 602 of the cardiac valve 600 and the fibrous tissue that surrounds cardiac valve prior to the cardiac valve 600 being implanted, as discussed above. In one embodiment, while implanting the first anchor frame 602 as discussed, the second inflatable balloon 688 remains in its deflated state at least partially positioned within the opening 632 of the second anchor frame 628 in its first predetermined configuration.

The second inflatable balloon 688 can then be implanted through the use of the second inflatable balloon 688. For example, upon implanting the first anchor frame 602 the first inflatable balloon 676 can be deflated. The first anchor frame 602 is still connected to the second anchor frame 628 with the struts 629. As a result, the second inflatable balloon 688 can be used to maintain pressure between the first anchor frame 602 and the tissue into which it is implanted by pulling on the delivery catheter 674. As the tension is being applied, the second inflatable balloon 688 can then be used to expand the second anchor frame 628 of the cardiac valve 600 into its fully deployed configuration.

In one embodiment, the second anchor frame 628 can be implanted into an artery or vein downstream of the first anchor frame 602. For example, the at least part of the delivery catheter 674 with the cardiac valve 600 could be positioned at a predetermined location such as in the region of the aortic valve. The first anchor frame 602 could be implanted adjacent the aortic valve, where the second anchor frame 628 would be positioned and implanted into the aorta of the patient. In an additional embodiment, the struts 629 would be sufficiently long enough so that the second anchor frame 628 would not interfere with the inlets to the coronary arteries, such as in the ascending aorta above the left and right coronary artery inlets. Other implant locations are also possible.

As will be appreciated, additional implantable medical devices might also be implanted in conjunction with the cardiac valve 600, as described herein. For example, cardiac stents might be placed in the coronary arteries adjacent their inlets from the aorta sinus. Stenting the arteries in this manner may help in maintaining their patent shape after the cardiac valve 600 has been implanted.

The embodiments of the valve described herein may be used to replace, supplement, or augment valve structures within one or more lumens of the body. For example, embodiments of the present invention may be used to replace an incompetent cardiac valve of the heart, such as the aortic, pulmonary and/or mitral valves of the heart. In one embodiment, the cardiac valve can either remain in place or be removed prior to implanting the cardiac valve discussed herein.

In addition, positioning the delivery catheter including the valve as discussed herein includes introducing the delivery catheter into the cardiovascular system of the patient using minimally invasive percutaneous, transluminal catheter based delivery system, as is known in the art. For example, a guidewire can be positioned within the cardiovascular system of a patient that includes the predetermined location. The delivery catheter, including valve, as described herein, can be positioned over the guidewire and the catheter advanced so as to position the valve at or adjacent the predetermined location. In one embodiment, radiopaque markers on the catheter and/or the valve, as described herein, can be used to help locate and position the valve.

The valve can be deployed from the delivery catheter at the predetermined location in any number of ways, as described herein. In one embodiment, valve of the present invention can be deployed and placed in any number of cardiovascular locations. For example, valve can be deployed and placed within a major artery of a patient. In one embodiment, major arteries include, but are not limited to, the aorta. In addition, valves of the present invention can be deployed and placed within other major arteries of the heart and/or within the heart itself, such as in the pulmonary artery for replacement and/or augmentation of the pulmonary valve and between the left atrium and the left ventricle for replacement and/or augmentation of the mitral valve. Other locations are also possible.

As discussed herein, the valve can be deployed from the catheter in any number of ways. For example, the catheter can include the retractable sheath in which valve can be at least partially housed, as discussed herein. Valve can be deployed by retracting the retractable sheath of the delivery catheter and extending the placement guides so that the valve expands to be positioned at the predetermined location. In an additional embodiment, the valve can be deployed through the use of one or more inflatable balloons, as discussed herein. In a further embodiment, the valve can partially self-expand upon retracting a sheath in which the valve is located, and then deployed through the use of an inflatable balloon.

Once implanted, the valve can provide sufficient contact with the body lumen wall to prevent retrograde flow between the valve and the body lumen wall, and to securely located the valve and prevent migration of the valve. The valve described herein also display sufficient flexibility and resilience so as to accommodate changes in the body lumen diameter, while maintaining the proper placement of valve. As described herein, the valve can engage the lumen so as to reduce the volume of retrograde flow through and around valve. It is, however, understood that some leaking or fluid flow may occur between the valve and the body lumen and/or through valve leaflets.

While the present invention has been shown and described in detail above, it will be clear to the person skilled in the art that changes and modifications may be made without departing from the spirit and scope of the invention. As such, that which is set forth in the foregoing description and accompanying drawings is offered by way of illustration only and not as a limitation. The actual scope of the invention is intended to be defined by the following claims, along with the full range of equivalents to which such claims are entitled.

In addition, one of ordinary skill in the art will appreciate upon reading and understanding this disclosure that other variations for the invention described herein can be included within the scope of the present invention. For example, the anchor frame(s) and/or the leaflets can be coated with a non-thrombogenic biocompatible material, as are known or will be known. Other biologically active agents or cells may also be utilized.

In the foregoing Detailed Description, various features are grouped together in several embodiments for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A cardiac valve prosthesis, comprising:
   only a first anchor frame consisting of a first single frame member that forms a ring around a common axis, where an infinitely vast plane parallel with and passing through the common axis and extending beyond an overall width and an overall height of the single frame member can only pass through two portions of the first single frame member to define a cross-sectional profile for each of the two portions having only one contiguous edge, and where the first single frame member has an inner portion defining an opening through the first anchor frame and an upper portion generally orthogonal to the inner portion;
   two or more leaflets coupled to the first anchor frame; and
   a pair of anchor members vertically extending from an apex of the first single frame member, the pair of anchor members restrained under tension in a first predetermined shape with a deployment member passing between the pair of anchor members, where the pair of anchor members moves toward a second predetermined shape when the deployment member is removed from between the pair of anchor members.

2. The cardiac valve of claim 1, wherein the pair of anchor members extend parallel with the common axis that is perpendicular to a common plane extending through the first anchor frame.

3. The cardiac valve of claim 1, wherein the pair of anchor members extend at an acute angle relative a common plane extending through the first anchor frame.

4. The cardiac valve of claim 1, wherein the first anchor frame expands from a first predetermined configuration to a fully deployed configuration.

5. The cardiac valve of claim 1, including a sealing material on the first anchor frame to prevent leakage of a liquid outside of the opening after anchoring the cardiac valve to tissue.

6. The cardiac valve of claim 5, wherein the sealing material expands in volume upon contacting the liquid.

7. The cardiac valve of claim 1, includes a sealing material positioned between the first anchor frame and deployment member, where upon removing the deployment member and anchoring the cardiac valve to tissue the sealing material prevents leakage of a liquid outside of the cardiac valve.

8. A cardiac valve prosthesis, comprising:
a first anchor frame having first single contiguous frame member that forms a ring around a common axis and has an inner portion defining an opening through the first anchor frame and an upper portion generally orthogonal to the inner portion, the first anchor frame having a plurality of apexes;
two of more leaflets coupled to the first anchor frame; and
two or more anchor members on each apex of the first single contiguous frame member, the two or more anchor members restrained under tension in a first predetermined shape with a deployment member passing between the two of more anchor members, where the two or more anchor members move towards a second predetermined shape when the deployment member is removed from between the two or more anchor members.

9. The cardiac valve prosthesis of claim 8, wherein the one or more anchor members extend parallel with the common axis.

10. The cardiac valve prosthesis of claim 8, wherein the one or more anchor members extend at an acute angle relative a common plane extending through the first anchor frame.

11. The cardiac valve prosthesis of claim 8, wherein the first anchor frame expands from a first predetermined configuration to a fully deployed configuration.

12. The cardiac valve prosthesis of claim 8, including a sealing material on the first anchor frame that prevents leakage of a liquid outside of the opening after anchoring the cardiac valve to tissue.

13. The cardiac valve prosthesis of claim 8, including a sealing material positioned between the first anchor frame and the deployment member, where upon removing the deployment member and anchoring the cardiac valve to tissue the sealing material prevents leakage of liquid outside of the opening of the cardiac valve.

* * * * *

UNITED STATES PATENT AND TRADEMARK OFFICE
CERTIFICATE OF CORRECTION

PATENT NO. : 8,512,399 B2
APPLICATION NO. : 12/648221
DATED : August 20, 2013
INVENTOR(S) : Daniel M. Lafontaine It is certified that error appears in the above-identified patent and that said Letters Patent is hereby corrected as shown below:

In the Claims

Column 19, Line 8, delete "of" and insert --or--.
Column 19, Line 13, delete "of" and insert --or--.

Signed and Sealed this
Twenty-second Day of October, 2013

Teresa Stanek Rea
*Deputy Director of the United States Patent and Trademark Office*